(12) United States Patent
Xu et al.

(10) Patent No.: US 11,208,355 B2
(45) Date of Patent: *Dec. 28, 2021

(54) METAL OXIDE CERAMIC NANOMATERIALS AND METHODS OF MAKING AND USING SAME

(71) Applicant: Ivoclar Vivadent AG, Schaan (LI)

(72) Inventors: Wei Xu, Basking Ridge, NJ (US);
Yijun Wang, Basking Ridge, NJ (US);
Dmitri Brodkin, Livingston, NJ (US)

(73) Assignee: Ivoclar Vivadent AG, Schaan (LI)

( * ) Notice: Subject to any disclaimer, the term of this patent is extended or adjusted under 35 U.S.C. 154(b) by 411 days.

This patent is subject to a terminal disclaimer.

(21) Appl. No.: 15/817,994

(22) Filed: Nov. 20, 2017

(65) Prior Publication Data
US 2018/0170812 A1 Jun. 21, 2018

Related U.S. Application Data

(60) Continuation of application No. 15/388,165, filed on Dec. 22, 2016, now Pat. No. 9,820,917, which is a (Continued)

(51) Int. Cl.
*C04B 35/48* (2006.01)
*C04B 35/486* (2006.01)
(Continued)

(52) U.S. Cl.
CPC .............. *C04B 35/486* (2013.01); *A61K 6/17* (2020.01); *A61K 6/818* (2020.01); *B01D 61/002* (2013.01);
(Continued)

(58) Field of Classification Search
CPC .... C04B 35/117; C04B 35/48; C04B 33/1315
See application file for complete search history.

(56) References Cited

U.S. PATENT DOCUMENTS 2,467,089 A * 4/1949 Griest .................... C01G 25/02
423/608
4,758,541 A 7/1988 Tsukuma
(Continued)

FOREIGN PATENT DOCUMENTS

EP 2692311 2/2014
WO 2014209626 12/2014

OTHER PUBLICATIONS

Adam et al. "Milling of Zirconia Nanoparticles in a Stirred Media Mill," J. Am. Ceram. Soc., 91 [9] 2836-2843 (2008).
(Continued)

*Primary Examiner* — Michael A Salvitti
(74) *Attorney, Agent, or Firm* — Hodgson Russ LLP

(57) ABSTRACT

Provided are metal oxide ceramic materials and intermediate materials thereof (e.g., nanozirconia gels, nanozirconia green bodies, pre-sintered ceramic bodies, zirconia dental ceramic materials, and dental articles). The nanozirconia gels are formable gels. Also provided are methods of making and using the metal oxide materials and intermediate materials. The nanozirconia gels can be made using, for example, osmotic processing. The nanozirconia gels can be used to make nanozirconia green bodies, pre-sintered ceramic bodies, zirconia dental ceramic materials, and dental article. The nanozirconia green bodies, pre-sintered ceramic bodies, zirconia dental ceramic materials, and dental articles have desirable properties (e.g., optical properties and mechanical properties).

12 Claims, 14 Drawing Sheets

Related U.S. Application Data division of application No. 15/240,673, filed on Aug. 18, 2016, now Pat. No. 9,822,039.

(51) Int. Cl.

| | | |
|---|---|---|
| *C04B 35/624* | (2006.01) | |
| *C04B 35/634* | (2006.01) | |
| *C04B 35/638* | (2006.01) | |
| *C01G 25/02* | (2006.01) | |
| *C08K 3/22* | (2006.01) | |
| *C08L 71/02* | (2006.01) | |
| *C02F 1/44* | (2006.01) | |
| *B01D 61/00* | (2006.01) | |
| *A61K 6/17* | (2020.01) | |
| *A61K 6/818* | (2020.01) | |
| *C04B 35/488* | (2006.01) | |
| *C02F 103/12* | (2006.01) | |

(52) U.S. Cl.
CPC .......... *B01D 61/005* (2013.01); *C01G 25/02* (2013.01); *C02F 1/445* (2013.01); *C04B 35/488* (2013.01); *C04B 35/4885* (2013.01); *C04B 35/624* (2013.01); *C04B 35/638* (2013.01); *C04B 35/63416* (2013.01); *C04B 35/63488* (2013.01); *C08K 3/22* (2013.01); *C08L 71/02* (2013.01); *B01D 2311/02* (2013.01); *B01D 2311/04* (2013.01); *C01P 2004/64* (2013.01); *C02F 2103/12* (2013.01); *C04B 2235/3217* (2013.01); *C04B 2235/5454* (2013.01); *C04B 2235/5463* (2013.01); *C04B 2235/602* (2013.01); *C04B 2235/606* (2013.01); *C04B 2235/608* (2013.01); *C04B 2235/61* (2013.01); *C04B 2235/612* (2013.01); *C04B 2235/762* (2013.01); *C04B 2235/765* (2013.01); *C04B 2235/77* (2013.01); *C04B 2235/781* (2013.01); *C04B 2235/785* (2013.01); *C04B 2235/96* (2013.01); *C04B 2235/9653* (2013.01)

(56) References Cited

U.S. PATENT DOCUMENTS

| | | | | |
|---|---|---|---|---|
| 4,963,264 | A * | 10/1990 | Davis | B01D 15/00 210/638 |
| 5,553,630 | A * | 9/1996 | Dupuis | A61K 8/19 132/202 |
| 6,232,367 | B1 | 5/2001 | Kobashigawa et al. | |
| 6,376,590 | B2 * | 4/2002 | Kolb | B01J 13/0008 106/287.19 |
| 6,787,080 | B1 | 9/2004 | Lange et al. | |
| 6,869,501 | B2 | 3/2005 | Davidson et al. | |
| 7,241,437 | B2 | 7/2007 | Davidson et al. | |
| 7,429,422 | B2 | 9/2008 | Davidson et al. | |
| 7,538,055 | B2 | 5/2009 | Tsukuma et al. | |
| 7,655,586 | B1 * | 2/2010 | Brodkin | B82Y 30/00 501/103 |
| 7,674,523 | B2 | 3/2010 | Davidson et al. | |
| 7,806,694 | B2 | 10/2010 | Brodkin et al. | |
| 7,833,621 | B2 | 11/2010 | Jones et al. | |
| 7,989,504 | B2 | 8/2011 | Adam et al. | |
| 8,216,439 | B2 | 7/2012 | Olevsky et al. | |
| 8,298,329 | B2 | 10/2012 | Knapp et al. | |
| 8,309,015 | B2 | 11/2012 | Rolf et al. | |
| 8,425,809 | B2 | 4/2013 | Ketharam et al. | |
| 8,598,058 | B2 * | 12/2013 | Mathers | C04B 35/62695 501/103 |
| 8,969,227 | B2 * | 3/2015 | Mathers | C04B 35/624 501/103 |
| 9,120,200 | B2 * | 9/2015 | Haerle | C09K 3/1409 |
| 9,657,152 | B2 | 5/2017 | Kolb et al. | |
| 9,820,917 | B1 * | 11/2017 | Xu | C04B 35/624 |
| 9,822,039 | B1 * | 11/2017 | Xu | A61K 6/17 |
| 2004/0222098 | A1 | 11/2004 | Clasen et al. | |
| 2008/0242746 | A1 * | 10/2008 | Morimura | C01G 25/02 516/90 |
| 2009/0004098 | A1 | 1/2009 | Schmidt et al. | |
| 2009/0074655 | A1 * | 3/2009 | Suciu | B82Y 30/00 423/608 |
| 2009/0115084 | A1 | 5/2009 | Moon | |
| 2009/0189115 | A1 | 7/2009 | Suciu | |
| 2009/0208746 | A1 | 8/2009 | Suciu | |
| 2009/0274993 | A1 | 11/2009 | Bergstrom et al. | |
| 2009/0294357 | A1 | 12/2009 | Binner et al. | |
| 2010/0003630 | A1 | 1/2010 | Yamashita et al. | |
| 2010/0075170 | A1 | 3/2010 | Adair et al. | |
| 2011/0027742 | A1 | 2/2011 | Fujisaki et al. | |
| 2011/0230340 | A1 | 9/2011 | Binner et al. | |
| 2012/0058883 | A1 | 3/2012 | Yamashita et al. | |
| 2012/0264588 | A1 * | 10/2012 | Kolb | C01G 25/00 501/134 |
| 2012/0277088 | A1 * | 11/2012 | Mathers | C04B 35/624 501/134 |
| 2013/0313738 | A1 | 11/2013 | Carden | |
| 2014/0057774 | A1 * | 2/2014 | Mathers | C04B 35/48 501/134 |
| 2014/0147387 | A1 * | 5/2014 | Butts | A61K 49/1848 424/9.1 |
| 2015/0238291 | A1 * | 8/2015 | Hauptmann | A61C 13/0006 428/64.1 |
| 2015/0328613 | A1 * | 11/2015 | Shi | C01G 25/02 516/33 |
| 2016/0095798 | A1 * | 4/2016 | Brodkin | A61C 13/083 428/402 |
| 2017/0231730 | A1 * | 8/2017 | Shen | A61C 13/26 433/201.1 |
| 2018/0170812 | A1 * | 6/2018 | Xu | C04B 35/486 |

OTHER PUBLICATIONS

Alaniz, J. E., et al. "Optical Properties of Transparent Nanocrystalline Yttria Stabilized Zirconia," Opt. Mater., 32, 62-68 (2009).

Anselmi-Tamburini, et al., "Transparent Nanometric Cubic and Tetragonal Zirconia Obtained by High-Pressure Pulsed Electric Current Sintering," Adv. Funct. Mater. 17, 3267-3273 (2007).

Apetz, R., et al., "Transparent Alumina: A Light Scattering Model," J. Am. Ceram. Soc., 86 [3], 480-786 (2003).

Binner, J., et al., "Processing of Bulk Nanostructured Ceramics," J. Eur. Ceram. Soc. 28, 1329-1339 (2008).

Binner, J., et al., "Compositional Effects in Nanostructured Yttria Partially Stabilized Zirconia," Int. J. Appl. Ceram. Tec., 8, 766-782 (2011).

Casolco, S.R. et al., "Transparent/translucent polycrystalline nanostructured yltria stabilized zirconia with varying colors," Scripta Mater. 58 [6], 516-519 (2007).

Garcia, et al., "Structural, Electronic, and Optical Properties of ZrO2 from Ab Initio Calculations," J. Appl. Phys., 100 [1], 104103 (2006).

Klimke, et al., Transparent Tetragonal Yttria-Stabilized Zirconia Ceramics, J. Am. Ceram. Soc., 94 [6] 1850-1858 (2011).

Knapp, K., "Understanding Zirconia Crown Esthetics and Optical Properties," Inclusive Magazine, (2011).

Rignanese, et al., "First-principles Study of the Dynamical and Dielectric Properties of Tetragonal Zirconia," Phys. Rev. B, 64 [13], 134301 (2001).

Srdic, V. V., et al. "Sintering Behavior of Nanocrystalline Zirconia Prepared by Chemical Vapor Synthesis," J. Am. Ceram. Soc. 83 [4], 729-736 (2000).

Srdic, V.V., et al., "Sintering Behavior of Nanocrystalline Zirconia Doped with Alumina Prepared by Chemical Vapor Synthesis," J. Am. Ceram. Soc. 83 [8], 1853-1860 (2000).

Trunec, et al., "Compaction and Presureless Sintering of Zirconia Nanoparticles," J. Am. Ceram. Soc. 90 [9] 2735-2740 (2007).

Cho, M.-S. et al., "Opalescence of all-ceramic core and veneer materials," Dental Materials, 25, 695-702 (2009).

(56) References Cited

OTHER PUBLICATIONS

Egen, M., et al., "Artificial Opals as Effect Pigments in Clear-Coatings," Macromol. Mater. Eng. 289, 158-163 (2004).
Lee, Y.-K., et al., "Measurement of Opalescence of Resin Composites," Dental Materials 21, 1068-1074 (2005).
Lee, Y.-K., et al., "Changes in Opalescence and Fluorescence Properties of Resin Composites after Accelerated Aging," Dental Materials 22, 653-660 (2006).
Lee, Y.-K, "Influence of Scattering/Absorption Characteristics on the Color of Resin Composites," Dental Materials 23, 124-131 (2007).
Lee, Y.-K, "Measurement of Opalescence of Tooth Enamel," Journal of Dentistry 35, 690-694 (2007).
White, et al., "Biological Organization of Hydroxyapatite Crystallites into a Fibrous Continuum Toughens and Controls Anisotropy in Human Enamel," J. Dent. Res. 80(1): 321-326, (2001).
Peelen, J. G. J. et al., "Light Scattering by Pores in Polycrystalline Materials: Transmission Properties of Alumina," Journal of Applied Physics, 45, 216-220 (1974).
Primus, C. M., et al., "Opalescence of Dental Porcelain Enamels," Quintessence International, 33, 439-449 (2002).
Yu, B., et al., "Difference in Opalescence of Restorative Materials by the Illuminant," Dental Materials 25, 1014-1021 (2009).
Kobashigawa, A. I. et al., "Opalescent Fillers for Dental Restorative Composites," U.S. Pat. No. 6,232,367 B1 (2001).
Dialysis, Obtained from https://www.merriam-webster.com/dictionary/dialysis on Jan. 8, 2017.
Schwartz et al., Introduction to Tangential Flow Filtration for Laboratory and Process Development Applications. Obtained from http://www.pall.com/main/laboratory/literature-library-details.page?id=34212 on Jan. 8, 2017.

\* cited by examiner

| Property | Drop cast green body of CoEx1 (no binder) | Gel-derived green body of Ex2A (1.0PEG35k) | Gel-derived green body of Ex3A (0.05PVA+1.0PEG) | Gel-derived green body of Ex5A (0.05PVA+0.1PEG) |
|---|---|---|---|---|
| Pore Volume (cc/g) | 0.095 | 0.061 | 0.068 | 0.083 |
| Modal Pore Diameter (nm) | 6 | 6 | 5 | 5 |
| Surface Area ($m^2$/g) | 65.3 | 43.1 | 59.8 | 74.5 |
| TODA added per surface area, mg/$m^2$ | 0.29 | 0.44 | 0.31 | 0.26 |
| Green Density in Percent of Theoretical Density (6.08 g/cc), % | 49-52 | 55-56 | 54-56 | 54-56 |

METAL OXIDE CERAMIC NANOMATERIALS AND METHODS OF MAKING AND USING SAME

CROSS-REFERENCE TO RELATED APPLICATIONS

This application is a Continuation application of U.S. patent application Ser. No. 15/388,165, filed on Dec. 22, 2016, now pending, which is a Divisional application of U.S. patent application Ser. No. 15/240,673, filed on Aug. 18, 2016, now pending, the disclosures of each of which are incorporated herein by reference.

FIELD OF THE DISCLOSURE

The disclosure generally relates to metal oxide ceramic materials. More particularly the disclosure generally relates to nanozirconia ceramic materials and formable nanozirconia gels.

BACKGROUND OF THE DISCLOSURE

The commercially available full contour (monolithic) Yttria-stabilized tetragonal zirconia polycrystal (Y-TZP) dental ceramics have been used as a dental restorative material for over a decade for their superior mechanical properties in spite of being aesthetically inferior with lower translucency and lack of opalescence compared to lithium disilicate or leucite-based glass ceramic materials like IPS e.max or IPS Empress. While increasing the amount of doped yttria could effectively reduce the opacity of Y-TZP, it significantly lowers its mechanical strength and limits its clinical use for multi-unit restorations. The solution to this dilemma is to use nano-sized zirconia particles and thus to make zirconia restoration containing mean grain size around 100 nm or less. Such nanozirconia would not only yield higher mechanical strength than conventional zirconia but also maximize Y-TZP's translucency by reducing the size of scattering centers.

The commercialization of nanozirconia dental restorations requires the ability to produce a viable nanozirconia body of bulk size (thickness is 10 mm or greater) with uniform microstructure. Such nanozirconia restorations have not been reported so far in literature and the dental industry lacks the technology for bulk shape consolidation. The current state of art of processing zirconia is not suitable for nanozirconia for at least some of the following reasons:
1. Dry processing methods are not applicable. Due to the inherent high specific surface area of nanoparticles, they are prone to strong agglomeration. This strong propensity to agglomerate can result in undesirable material properties when processed using typical manufacturing methods for conventional zirconia such as die pressing.
2. Most of liquid processing methods are not applicable. For example, slip casting of nanozirconia suspension is not able to produce thick bodies due to its low suction power associated with capillary force of molds. Direct coagulation casting would introduce inhomogeneities and requires high solid loading prior to casting stages. Gel casting methods use large amount of organics and later cause difficulty during debinding. Centrifugal consolidation from suspension is subject to non-uniformities of solid loading/relative density in the bulk because of the segregation of nanoparticles of different sizes.

Liquid processing methods from colloidal suspension are still a useful approach to produce viable dental articles despite two technical challenges to make mass manufacturing nanozirconia possible. First, to invent techniques of consolidating and drying bulk shapes with uniform/homogenous structure at the nano scale in each processing step; second, to invent techniques of processing bulk shape after casting, which include removing unwanted water and any processing agents during drying and debinding through extremely small pores/channels (pore size less than 10 nm) while maintaining the integrity of the nanozirconia bodies.

SUMMARY OF THE DISCLOSURE

The present disclosure provides metal oxide ceramic materials and intermediate materials thereof. The present disclosure also provides methods of making and using the metal oxide materials and intermediate materials. Examples of metal oxide ceramic materials and intermediate materials include, but are not limited to, nanozirconia gels, nanozirconia green bodies, pre-sintered ceramic bodies, zirconia dental ceramic materials, and dental articles.

The metal oxide materials (e.g., zirconia dental ceramic materials, and dental articles) and other intermediate materials (e.g., nanozirconia green bodies, pre-sintered ceramic bodies) can be made from a gel of the present disclosure. The gels are formable gels, which can be formed into a three-dimensional shape (e.g., a free-standing three-dimensional shape) and subjected to further processes to provide metal oxide materials (e.g., zirconia dental ceramic materials and dental articles) and other intermediate materials (e.g., nanozirconia green bodies, pre-sintered ceramic bodies) of the present disclosure having desirable features (e.g., crack-free metal oxide materials and other intermediate materials).

In an aspect, the present disclosure provides gels. The gels can be formable gels. The gels comprise nanozirconia and water. The gels comprise a plurality of zirconia nanoparticles. The nanozirconia can have an average size of 10 to 30 nm, including all integer nm values and ranges therebetween. The nanozirconia can have various size distributions. The nanozirconia is uniform and homogenous (e.g., well-dispersed) within the gel. The gel can have various nanozirconia loadings. The gel can comprise a processing agent. The gel can comprise a combination of processing agents. The gels have desirable optical characteristics (e.g., translucency and/or opalescence). The gel has desirable physical properties. A gel is redispersible in an aqueous medium (e.g., water).

In an aspect, the present disclosure provides zirconia green bodies. The zirconia green bodies can be made by removal of water from a formable nanozirconia gel of the present disclosure (e.g., a shaped formable nanozirconia gel of the present disclosure). The zirconia green body comprises a plurality of zirconia nanoparticles. The nanozirconia can have various size distributions. The zirconia green body is porous. In various examples, the zirconia green body has a surface area of 40 to 80 $m^2/g$, including all integer $m^2/g$ values and ranges therebetween. The zirconia green body can comprise water. The zirconia green body can comprise a processing agent. The zirconia green body can comprise a combination of processing agents. The zirconia green body has desirable optical characteristics (e.g., translucency and/or opalescence). The zirconia green body has desirable physical properties. The zirconia green body can have various shapes and/or sizes.

In an aspect, the present disclosure provides pre-sintered ceramic bodies. The pre-sintered ceramic bodies can be made from zirconia green bodies of the present disclosure. The pre-sintered ceramic bodies are porous. The pre-sintered ceramic bodies comprise a plurality of zirconia nanoparticles. The pre-sintered body has desirable optical characteristics (e.g., translucency). For example, where pre-sintered body is translucent and has a transmittance at 560 nm wavelength of 40 to 60% for a 1 to 2 mm thick sample of the pre-sintered ceramic body. The pre-sintered body can have various shapes and/or sizes. In various examples, the pre-sintered body has a longest dimension of 15 to 100 mm, including all integer nm values and ranges therebetween. In various examples, the pre-sintered body has a dimension of 10 to 30 mm, including all integer nm values and ranges therebetween, in a direction perpendicular to the longest dimension of the pre-sintered body (thickness).

In an aspect, the present disclosure provides zirconia dental ceramic materials. The zirconia dental ceramic can have at least 95% of all grains by volume have a size of 10 to 300 nm and/or the average grain size is 40 to 150 nm and/or the density of the zirconia dental ceramic has a density that is at least 99.5% of zirconium dioxide theoretical density. The zirconia dental ceramic has desirable optical characteristics (e.g., translucency and/or opalescence). The zirconia dental ceramic has desirable physical properties.

In an aspect, the present disclosure provides dental articles. The dental articles can be comprised of zirconia ceramic materials of the present disclosure. The dental articles can be made from pre-sintered bodies of the present disclosure. For example, the dental article is a blank (e.g., a simple shape) or smart blank (e.g., a shape closer to the final shape of a dental restoration). For example, the dental article is a dental restoration.

In an aspect, the present disclosure provides methods of making gels (e.g., gels of the present disclosure). The methods are based on the removal of water from an aqueous suspension of zirconia nanoparticles using a semipermeable membrane (e.g., using osmotic processing or tangential flow processing). Water can be removed from the aqueous suspension using an intrinsically induced pressure (e.g., an osmotic process) or externally imposed pressure (e.g., a tangential flow process). The water removal process (e.g., a portion of or all of the process) can be carried out with physical agitation (e.g., shaking or stirring) of the aqueous suspension. The water can be removed without use of an exogenous heat source. The aqueous suspension can further comprise a processing agent. A method of making a gel can comprise attrition milling a starting aqueous suspension and, optionally, subjecting the attrition milled starting aqueous suspension to centrifugation.

In an aspect, the present disclosure provides methods of making zirconia green bodies. The methods are based on the removal of water (e.g., non-equilibrium water) from a gel (e.g., a gel that has been shaped into a desired shape). The water can be removed by holding a gel (e.g., a shaped gel) in a controlled-humidity and controlled-temperature environment (e.g., in multiple controlled-humidity and controlled-temperature environments having different humidity and temperature).

In an aspect, the present disclosure provides methods of making pre-sintered ceramic bodies. The methods are based on heating a zirconia green body. During the heating organic materials (e.g., processing agent(s)) are removed from a zirconia green body.

In an aspect, the present disclosure provides methods of making dental articles. The methods are based on shaping and heating a pre-sintered ceramic body or zirconia green body.

BRIEF DESCRIPTION OF THE FIGURES

For a fuller understanding of the nature and objects of the disclosure, reference should be made to the following detailed description taken in conjunction with the accompanying figures.

DETAILED DESCRIPTION OF THE DISCLOSURE

Figure 1:
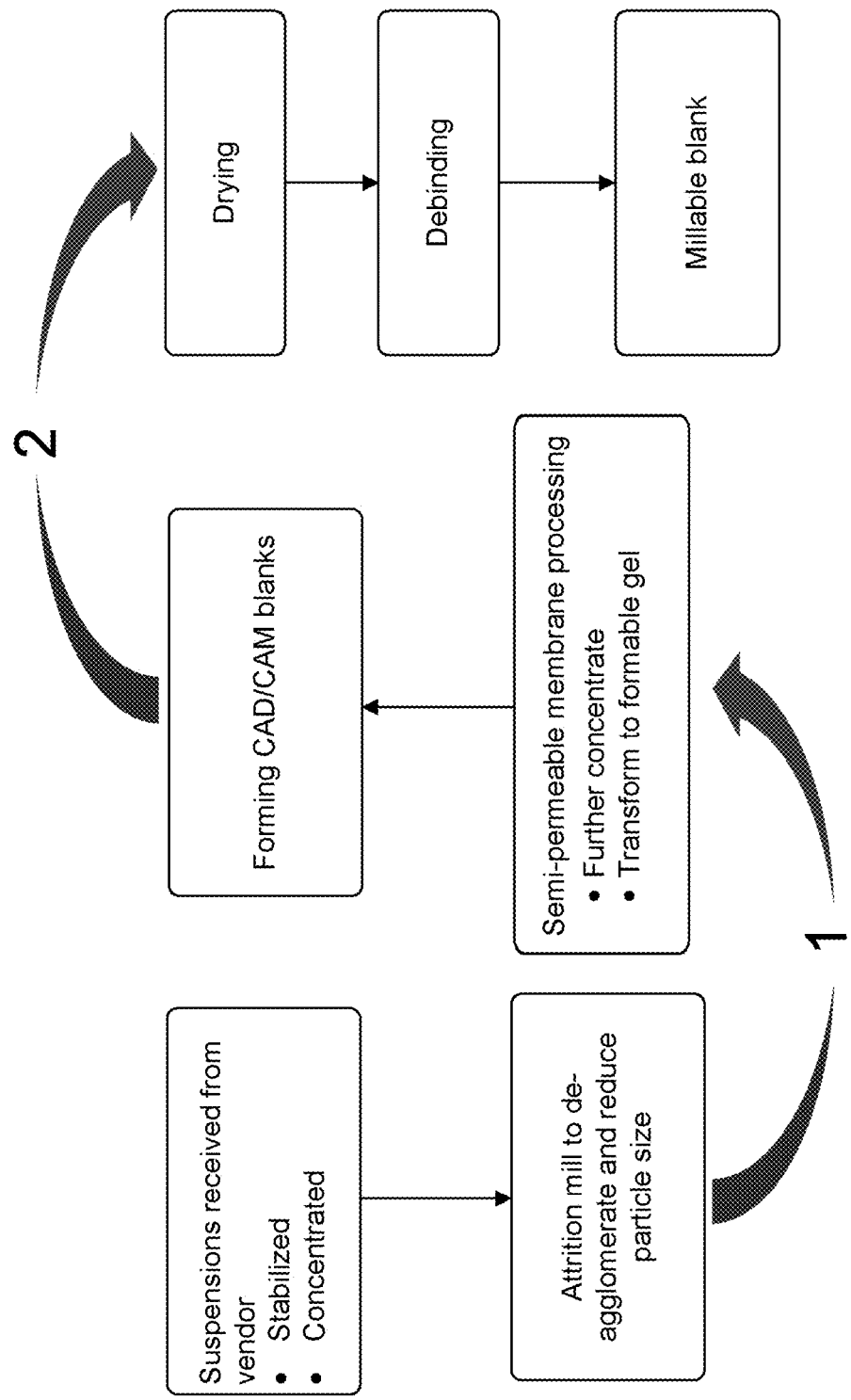
FIG. 1. Example of generalized nanozirconia processing flowchart.

Although claimed subject matter will be described in terms of certain examples and embodiments, other examples and embodiments, including examples and embodiments that do not provide all of the benefits and features set forth herein, are also within the scope of this disclosure. Various structural, logical, and process step changes may be made without departing from the scope of the disclosure.

All ranges provided herein include all values that fall within the ranges to the tenth decimal place, unless indicated otherwise. The numbers and ranges in the specification and claims can cover values obtained by applying the regular rules of rounding and/or up to +/−5%.

The present disclosure provides metal oxide ceramic materials and intermediate materials thereof. The present disclosure also provides methods of making and using the metal oxide materials and intermediate materials. Examples of metal oxide ceramic materials and intermediate materials include, but are not limited to, nanozirconia gels, nanozirconia green bodies, pre-sintered ceramic bodies, zirconia dental ceramic materials, and dental articles.

The metal oxide materials (e.g., zirconia dental ceramic materials, and dental articles) and other intermediate materials (e.g., nanozirconia green bodies, pre-sintered ceramic bodies) can be made from a gel of the present disclosure. The gels are formable gels, which can be formed into a three-dimensional shape (e.g., a free-standing three-dimensional shape) and subjected to further processes to provide metal oxide materials (e.g., zirconia dental ceramic materials and dental articles) and other intermediate materials (e.g., nanozirconia green bodies, pre-sintered ceramic bodies) of the present disclosure having desirable features (e.g., crack-free metal oxide materials and crack-free intermediate materials, and intermediate materials having a thickness of 10 mm or greater).

It was unexpectedly found that constant shaking of the suspension during water removal (e.g., osmotic processing) provided a homogenous gel and minimal cavitation. It was also unexpectedly found that use of a various processing agents and combinations of processing agents provided metal oxide ceramic materials and intermediate materials with desirable properties. For example, use of colloid stabilizers prevented the formation of undesirable agglomeration, which can led to crack formation (e.g., in a zirconia green body), and/or particle interaction strengthening agents, which can enhance the attractive interaction among particles during drying process, can prevent cracking (e.g., in a zirconia green body).

This disclosure is related to, for example, processing of commercially available nanozirconia suspensions into formable nanozirconia gels via osmotic processing, and then to millable blanks and other dental articles by high throughput mass-production forming technologies like CIP, centrifugal casting or vibra-forming. Specifically, nanozirconia CAD/CAM blanks millable into a variety of dental articles and appliances can be provided in green, "brown", and "brown"/pre-sintered state.

The term "pre-sintering" (and its derivatives) means the same and can be used interchangeably with a term "soft-sintering." Compared to conventional dental zirconia blanks which are commercially available in pre-sintered state and in the past were also available in the green state, millable nanozirconia blanks of this disclosure can be also available in "brown" state, a term used herein to describe condition after burning out organics from green body without noticeable shrinkage/densification. This is possible because green and thus brown nanozirconia bodies of this disclosure already have high densities and millability comparable or exceeding commercial pre-sintered zirconia blanks. The methods described herein allow to produce millable blanks in a variety of shapes and sizes, for example, with thicknesses in the range of 10 to 30 mm. Nanozirconia blanks of this disclosure can be also provided in a near net shape approximating final shape of a dental article, i.e., as smart blanks which can be optionally sintered to full density to reduce material waste and eliminate sintering step.

Figure 2:
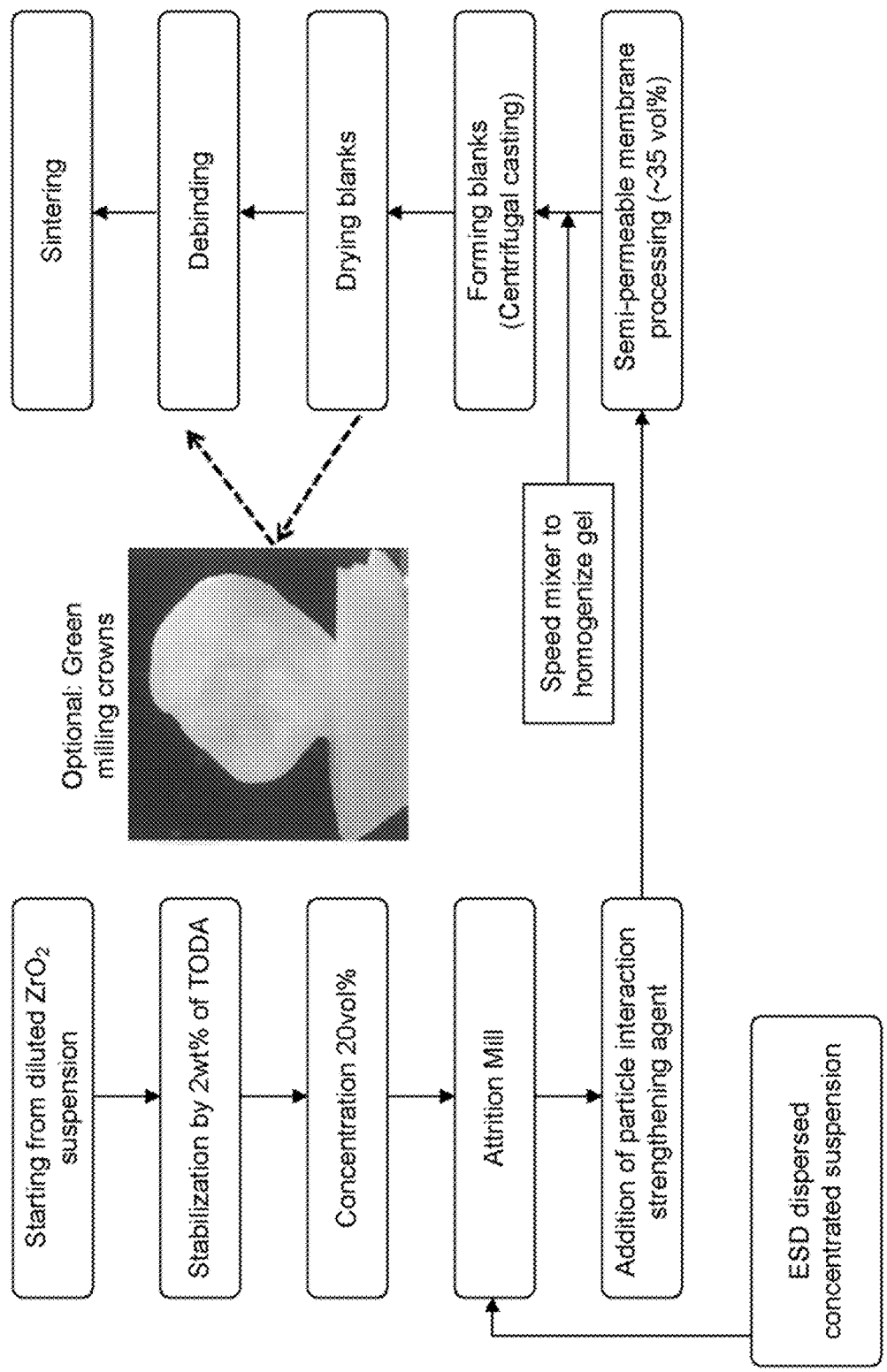
FIG. 2. Exemplary nanozirconia processing flowchart.
Figure 3:
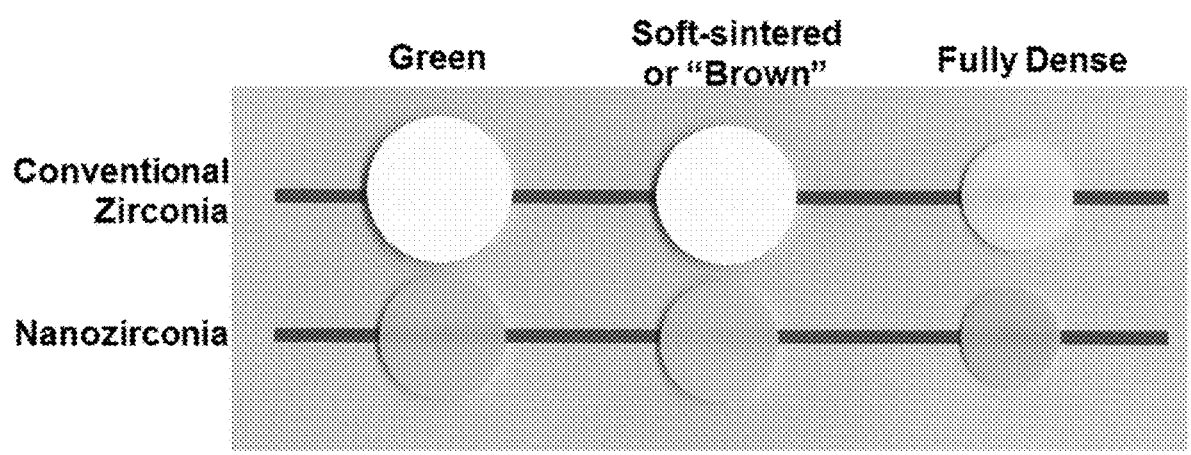
FIG. 3. Difference between conventional zirconia (PRIOR ART) and an example of nanozirconia.
Figure 4:
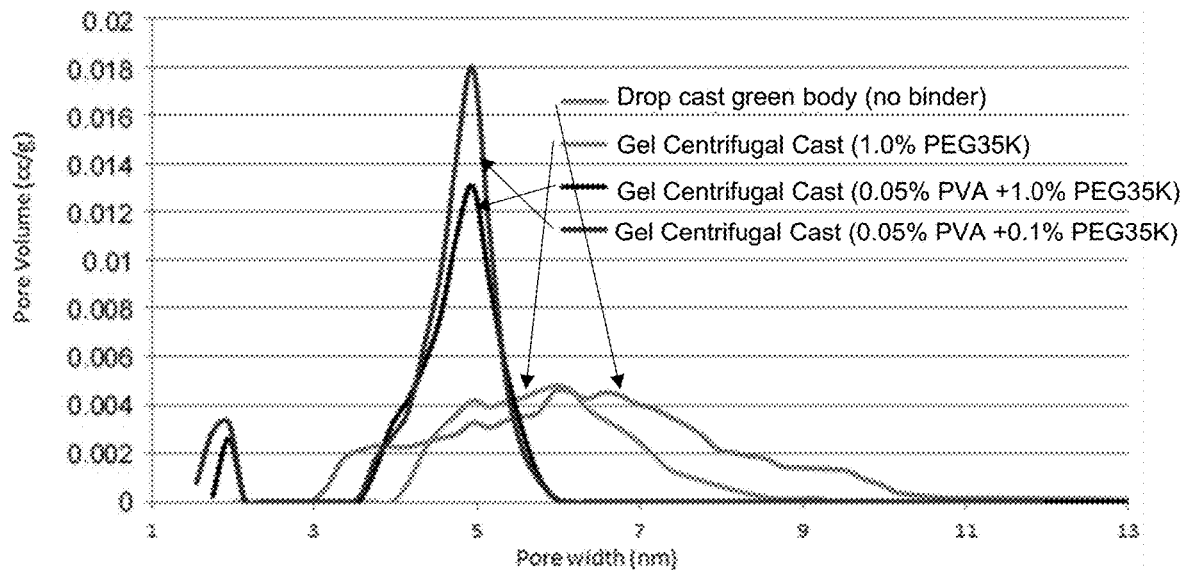
FIG. 4. Examples of pore size distribution and green density.

FIG. 1 shows generalized nanozirconia processing flow chart for commercial scale process starting from the stabilized and concentrated suspensions. FIG. 2 shows laboratory scale nanozirconia processing flow chart starting from the diluted suspensions. A method shown in FIG. 2 also allows milling in green state (or "green milling") and optional use of stabilized concentrated starting suspensions. FIG. 3 compares green, "brown"/pre-sintered (after organic burn-out) and fully dense nanozirconia to conventional zirconia (PRIOR ART) in comparable state in terms of translucency. Osmotic processing combined with forming by high throughput mass-production technologies like CIP, centrifugal casting or vibra-forming as taught in the present disclosure resulted in green bodies characterized by noticeably higher green densities and narrower pore size distribution than drop cast samples (PRIOR ART described in, for example, Comparative Example 1) samples leading initially to greater difficulties in drying and organic burn-out as water vapor and gaseous byproducts of decomposing organic additives should escape through a network of nanoscale channels, for example, with a diameter of less than 10 nm—see FIG. 4. Narrower channels filled with moisture are also associated with higher capillary forces making drying and organic burn out even more challenging, especially for relatively thick samples (e.g., samples having a thickness of 10 mm or greater).

Figure 5:
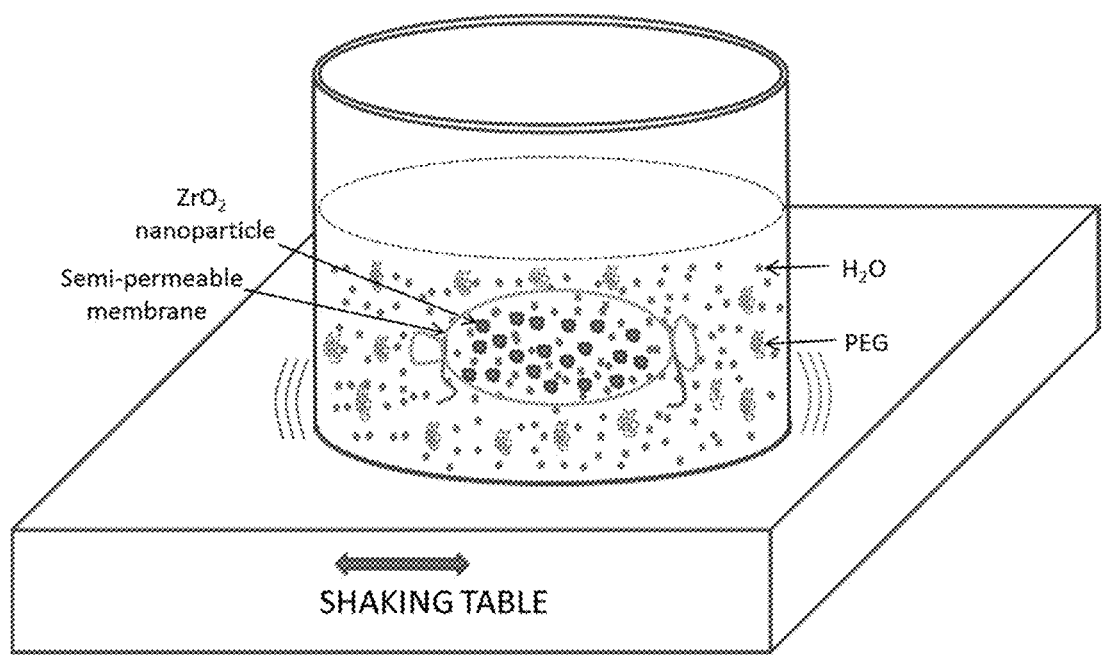
FIG. 5. Schematic of an example of an osmotic processing set-up.

It was unexpectedly found that processing improvements (such as constant agitation/shaking of membrane bag or the whole osmotic bath during osmotic processing as shown in FIG. 5) combined with certain organic additives (processing agents) provide uniform gels, which are capable of surviving drying and form crack-free green bodies and organic burn out in thicknesses of 10 to 30 mm consistent with commercial CAD/CAM blank dimensions. Hence the concept of resilient green bodies is introduced in the present disclosure to separate from conventional nanozirconia green bodies. It was found that to successfully burn out organics from nanozirconia green bodies their total organic content (including processing agents) should be under 3.1 wt. %.

It was also unexpectedly found that these green bodies can be milled in green state resulting in realistic crowns and bridges while their processing agent content (e.g., particle strengthening agent) was only from 0.1 to 1.1% by weight based on total weight of the nanoparticles in the green body (e.g., with additional processing agent(s), such as, for example, 2% by weight based on total weight of the nanoparticles in the green body TODA and/or ESD) indicating completely different mechanism than in conventional binder systems used in the current state of the art commercial zirconia with binder/plasticizer content of 3 to 5 wt. %. For example, green bodies having compositions comprising only 0.15% by weight based on total weight of the nanoparticles in the green body of processing agents used in conventional zirconia as binders (0.1% PEG35K+0.05% PVA9k) were successfully milled, which challenges applicability of conventional terminology of "binder/plastisizer" to process and materials of this disclosure. Without intending to be bound by any particular theory, it is considered that the millability of the green bodies is a result of the increased density and/or increased hardness of green bodies of the present disclosure compared to conventional zirconia green bodies.

It is noteworthy that desirable translucency is maintained through all stages of the processing from translucent suspensions to translucent gel to translucent green bodies to translucent brown or pre-sintered bodies to translucent fully sintered bodies. It was found out that high translucency is important visual indicator of the success of all the intermediate steps characteristic of the present disclosure.

In an aspect, the present disclosure provides gels. The gels are formable gels. The gels comprise nanozirconia and water. The gels can be made by a method of the present disclosure. In an example, a gel is made by a method of the present disclosure.

The gels comprise a plurality of zirconia nanoparticles. Zirconia nanoparticles are also referred to herein as nanozirconia. The nanozirconia in a gel can have a zirconium dioxide nominal composition comprising at least 91 wt % of $ZrO_2$ or at least 99% wt % of $ZrO_2$ wt %+$HfO_2$ wt %+$Y_2O_3$ wt %+$Al_2O_3$ wt %. The nanozirconia can be doped (e.g., yttria doped, alumina doped, or combinations thereof). For example, the zirconia nanoparticles can be yttria-stabilized YTZP zirconia nanoparticles comprising from 1 to 3 mol % of yttria ($Y_2O_3$) (e.g., 1Y, 2Y, or 3Y, where 1Y corresponds to about 1.7 to 1.8 wt % of $Y_2O_3$, 2Y to about 3.3 to 3.7 wt % of $Y_2O_3$, and 3Y to about 5.0 to 5.5 wt % of $Y_2O_3$). For example, the yttria content is 2 mol % or less (e.g. 1.5 to 2 mol %). In another example, the yttria content is 2.5 mol % or greater (e.g., 2.5 to 3 mol %). For example, the zirconia nanoparticles can be yttria-stabilized YTZP zirconia nanoparticles doped with alumina ($Al_2O_3$), where the alumina comprises 0.05 to 0.3 weight % based on the total nanoparticle weight. Without intending to be bound by any particular theory, it is considered that yttria content can be selected (e.g., 1.5 to 2 mol %) to provide desirable strength or selected (e.g., 2.5 to 3 mol %) to provide desirable translucency of the materials (e.g., dental material) made using the gel. Suitable nanozirconia is commercially available and can be made by methods known in the art.

Other optional oxides that may be present in gels as described herein (e.g., as optional components of the nanozirconia particles, coating(s) on the nanozirconia particles, or aqueous component of the gel) include, but are not limited to, $HfO_2$, $CeO_2$, $Pr_2O_3$, $Nd_2O_3$, $Tb_2O_3$, $Er_2O_3$, $Fe_2O_3$, $MnO_2$, $Co_2O_3$, $Cr_2O_3$, NiO, CuO, $Bi_2O_3$, $SiO_2$, and combinations thereof. Specific additives that may add desired coloring to the resulting nanozirconia ceramic or nanozirconia articles (e.g., coloring oxides) include, for example, $CeO_2$, $Pr_2O_3$, $Nd_2O_3$, $Tb_2O_3$, $Er_2O_3$, $Fe_2O_3$, $MnO_2$, $Co_2O_3$, $Cr_2O_3$, NiO, CuO, $Bi_2O_3$, and combinations thereof. In an example, the amount of coloring oxide(s) is in an amount in a range of about 10 ppm to 10,000 ppm, including all integer ppm values and ranges therebetween. In another example, the amount of coloring oxide(s) is in an amount in a range of about 20 ppm to 1,000 ppm. In some embodiments, it is desirable to have sufficient oxides present such that the nanozirconia ceramic or nanozirconia articles have coloring matching natural dentition, shade standards such as, for example, Ivoclar's MO1-MO4 shade standards, or shade standards such as, for example, Ivoclar Vivadent Chromascop or Vita classical Shade guides. Other additives such as, for example, compounds comprising rare earth elements and/or comprising lanthanum group elements can be added to impart fluorescence and/or modify opalescence of nanozirconia. While the dopants above are described as oxides for convenience, after sintering to full density they will be present as ions (e.g., within the zirconia crystal lattice or in intergranular phases) and their final content in the resulting nanozirconia article will be given on oxide basis. Initially they can be added as, for example, salts, colloids, organometallic compounds, ionic solutions, and the like, and therefore are referred to as additives.

Nanozirconia ceramics and nanozirconia articles (e.g., shaded nanozirconia) can be doped with coloring ions such as, for example, Pr ions, Fe ions, Cr ions, Ni ions, Co ions, Er ions, Mn ions, Tb ions, Nd ions, Ti ions, Cu ions, Bi ions, or a combination thereof to match colors of human dentition. Base shade zirconia can comprise the baseline levels of some or all of the oxides in the table below. Typically, light transmittance of shaded zirconia is 5 to 50% lower than light transmittance of unshaded or "naturally colored" or base-shade zirconia. Coloring ions can be added at any point during the fabrication process. For example, coloring ions can be added during any of the steps outlined in FIGS. 1 and 2, prior to forming of the CAD/CAM blanks or shaping gel. For example coloring can be achieved by adding ionic solutions comprising these elements before, during, or after the attrition milling step (see, e.g., FIG. 1). It may be desirable to add coloring ions prior to semi-permeable membrane processing step. In another example, water-soluble salts are added (e.g., using a speed mixer, which can assist in homogenizing the gel and can result in the salts being dissolved in the aqueous component of the gel) following a semi-permeable membrane processing step (see, e.g., FIG. 2).

Example of baseline level of selected other optional oxides in nanozirconia:

| | |
|---|---|
| $HfO_2$ | ≤30000 ppm |
| $SiO_2$ | ≤100 ppm |
| $TiO_2$ | ≤20 ppm |
| $Fe_2O_3$ | ≤20 ppm |
| $Na_2O$ | ≤50 ppm |
| NiO | ≤20 ppm |
| $Cr_2O_3$ | ≤20 ppm |
| $Ce_2O_3$ | ≤20 ppm |

The nanozirconia in a gel can have an average size of 10 to 30 nm, including all integer nm values and ranges therebetween. The average size of the nanoparticles can be determined by methods known in the art. For example, the average size of the nanoparticles is determined by dynamic light scattering (DLS) and when DLS is used to determine nanoparticle size, the size is an equivalent size. For example, the average size of the nanoparticles is determined by electron microscopy (e.g., transmission electron microscopy). When electron microscopy is used to determine nanoparticle size, the term "size" can mean the longest dimension of the nanoparticles.

The nanozirconia in a gel can have various size distributions. For example, 95% or more of the zirconia nanoparticles by volume (of the nanoparticles in the formable gel) have a size of 45 nm or less. In various examples, 96% or more, 97% or more, 98% or more, or 99% of the zirconia nanoparticles by volume have a size of 45 nm or less and/or 99% or more or 99.5% or more of the zirconia nanoparticles by volume have a size of 70 nm or less. In another example, i) 99% of nanoparticles by volume have a size less than 60 nm±10 nm; ii) 95% of nanoparticles by volume have a size less than 40 nm±5 nm; iii) 50% of nanoparticles by volume have a size less than 20 nm±5 nm; and iv.) 5% of nanoparticles by volume have a size less than 12 nm±3 nm.

The nanozirconia is uniform and homogenous (e.g., well-dispersed) in the gel. For example, 95% or greater by volume of the zirconia nanoparticles in a gel comprise 1 to 5 crystallites. In various examples, a gel has less than 2% or less than 1% agglomerates (e.g., agglomerates comprising greater than 5 crystallites) by volume based on the total volume of the gel (e.g., 1 to 2% by volume).

The gels can have various nanozirconia loadings. For example, the zirconia nanoparticles are present in the gel at 70 to 85% by weight based on the total weight of the gel. In various examples, the zirconia nanoparticles are present in the gel at 73 to 83% by weight or 75 to 81% by weight, based on the total weight of the gel. In an example, the zirconia nanoparticles are present in the gel at 28 to 48% by volume based on the total volume of the gel. In various examples, the zirconia nanoparticles are present in the gel at 31 to 44% or 33 to 41% by volume based on the total volume of the gel.

The gels can comprise a processing agent. The gel can comprise a combination of processing agents. Various amounts of processing agent(s) can be used. In various examples, the amount of the processing agent is 1.5 to 3.3% by weight, including all 0.1% by weight values and ranges therebetween, based on the total weight of the nanoparticles in the gel. In various example, the amount of the processing agent is 1.7 to 3.1% by weight or 2 to 2.6% by weight, based on the total weight of the nanoparticles in the gel. In various example, the processing agent comprises (or is) a particle interaction strengthening agent or combination of such agents and the amount of the particle interaction strengthening agent(s) is 0.15 to 1.05% by weight or 0.15 to 0.55% by weight, based on the total weight of the nanoparticles in the gel. Suitable processing agents are commercially available and can be made by methods known in the art.

Examples of suitable processing agents include, but is not limited to, of colloid stabilizers, particle interaction strengthening agents, and combinations thereof.

Examples of suitable particle interaction strengthening agents include, but are not limited to, polymer such as polyethylene glycol (PEG), polyethylene oxide (PEO), polyvinylalcohol (PVA), methyl cellulose, polyacrylic acid, dextrin, poly-ethylene-co-propylene-glycol, and combinations thereof. The polymers can have various molecular weights. In various examples, the polymer has a molecular weight (Mw) of 2,000 to 200,000 g/mol, including all integer g/mol values and ranges therebetween. In various other examples, the polymer has a molecular weight (Mw) of 5,000 to 100,000 g/mol or 8,000 to 40,000 g/mol.

Examples of suitable colloid stabilizers include, but are not limited to, dispersants, protective colloids, and combinations thereof. Colloid stabilizers can be steric colloid stabilizers. Colloid stabilizers can be electrosteric colloid stabilizers and/or electrostatic colloid stabilizers. Examples of colloid stabilizers also include, but are not limited to, organocarboxylic acids and salts thereof, polyoxocarboxylic acids and salts thereof (e.g., $CH_3$-[O—$(CH_2CH_2)$]$_x$$CO_2H$ and salts thereof, where x is 1 to 120, including all integer values and ranges therebetween), amino acids and salts thereof, organoamines and ammonium salts thereof, organoalcohols, organosilanes, and combinations thereof. In various examples, the polyoxocarboxylic acids have the following structure: $CH_3$-[O—$(CH_2CH_2)$]$_x$$CO_2H$ structure or salts thereof, where x is 1 to 50 or 1 to 30.

Examples of electrosteric colloid stabilizers and/or electrostatic colloid stabilizers, include, but are not limited to, 2-[2-(2-methoxyethoxy)ethoxy]acetic acid (TODA), 2-(2-methoxyethoxy)acetic acid (DOHA), O-(2-carboxyethyl)-O'-methyl-undecaethylene glycol, methoxypolyethylene glycol propionic acid (e.g., having a molecular weight of 5,000), 3,6,9-trioxaundecanedioic acid, and polyacrylic acid, bicine, dodecyl amine, tetradecyl methyl amine, cetyl trimethyl ammonium bromide (CTAB), ammonium polyacrylate, polyethylene glycol dodecyl ether, trimethoxy(propyl)silane, 2-[(acetoxy(polyethyleneoxy)propyl]triethoxysilane, 2-[methoxy(triethyleneoxy)propyl]trimethoxysilane, and combinations thereof. In various examples, methoxypolyethylene glycol propionic acids have the following structure:

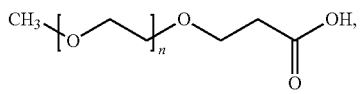

where n is 1 to 120, including all integer values and ranges therebetween. In various examples, n is 1 to 50 or 1 to 30.

Examples of electrostatic colloid stabilizers, include, but are not limited to acids, such as, for example, nitric acid, HCl, and carboxylic acids (e.g., acetic acid, citric acid, and oxalic acids) and bases such as, for example, ammonium hydroxide, tetraalkylammonium hydroxides (e.g., tetramethylammonium hydroxide), ethylenimine, urea, and salts, such as, for example, ammonium citrates (e.g., triammonium citrate and diammonium citrate), tetraalkylammonium chlorides (e.g., methylammonium chloride), ammonium chloride, ammonium carbonate. Electrostatic colloid stabilizers can be referred to herein by ESD.

The processing agent can comprise a steric colloid stabilizer/electrosteric colloid stabilizer (e.g., TODA) and/or an electrostatic colloid stabilizer (e.g., an ESD). For example, the processing agent is 2% by weight TODA and/or ESD and 0.1% by weight PEG (e.g., PEG having a molecular weight of 35K (PEG35k)) and 0.05% by weight PVA or 0.5% percent by weight PEG (e.g., PEG having a molecular weight of 35K (PEG35k)) and 0.05% by weight PVA, where the percent by weight values are based on the total weight of the nanoparticles in the gel.

The processing agent can be covalently bound to the nanozirconia in the gel. For example, at least a portion of the processing agent is attached via at least one covalent bond to at least a portion of the zirconia nanoparticles in the gel. For example, the processing agent is attached to a zirconia nanoparticle by one or more nanoparticle surface Zr—O—bond.

Gels have desirable optical characteristics (e.g., translucency and/or opalescence). For example, the gel is translucent and has a transmittance at 560 nm wavelength of 60 to 80% for a 1 to 2 mm thick sample of the gel and/or the gel has an opalescence of 20 to 30 for a 1 to 2 mm thick sample of the gel.

Transmittance of any of the materials of the present disclosure can be measured using methods known in the art. For example, total forward transmittance measurement was measured using integrating spheres. To collect all transmitted light, samples were placed up to the input port of the integrating sphere. When light strikes samples, integral detectors collect light and calculate the total forward transmittance in the spectrum range of visible wavelength.

The degree of opalescence (opalescence value) of any of the materials of the present disclosure can be quantified by methods known in the art. For example, the opalescence value is determined by a colorimetric spectrophotometry measurement with a CIE (Commission Internationale d'Eclairage) standard. For example, "Opalescence Parameter" (OP) or "Chromaticity Difference" are used as a measure of opalescence. The opalescence parameter (OP or "Chromaticity Difference") is calculated according to the following formula: $OP=[(CIEa_T{*}-CIEa_R{*})^2+(CIEb_T{*}-CIEb_R{*})^2]^{1/2}$, wherein $(CIEa_T{*}-CIEa_R{*})$ is the difference between transmission and reflectance modes in red-green coordinate a*; $(CIEb_T{*}-CIEb_R{*})$ is the difference between transmission and reflectance modes in yellow-blue color coordinate b*. Opalescence or transmittance can be determined using a 1 to 2 mm thick sample.

A gel is redispersible in an aqueous medium. For example, a gel is redispersible in water. By "redispersible" it is meant that the zirconia nanoparticles of the gel after resuspension in an aqueous medium have an average size or Dv50 that is within 2 nm or 10%, respectively, of the average size or Dv50 of the gel before redispersion (e.g., of the suspension used to make the suspension).

The gels are formable gels. By "formable" it is meant that the gel can be formed into a three-dimensional shape. The gel can be formed into a free-standing three-dimensional shape. The gels can be formed into three dimensional shapes, such as, for example, platonic solids, prisms, pyramids, spheres, cylinders, cones, discs, and any portion thereof. The gels can also be formed into the shape (or approximate shape to account for shrinkage of the gel on drying and further processing) of a dental article. For example, a formable gel of the present disclosure is formable into the desired shape (e.g., by centrifugal force, vibration, pressure, or a combination thereof) and capable of losing water in a controlled-humidity and controlled-temperature environment without cracking while maintaining the shape integrity, whereby a zirconia green body having 2% to 5% water based on the weight of the zirconia green body is formed.

A gel can be reversibly shaped. A gel can be shaped and subsequently reshaped (e.g., reshaped into a different shape).

The gel has desirable physical properties. For example, the gel exhibits a viscosity at yield point of $1 \times 10^9$ to $12 \times 10^9$ mPa·s. In various examples, the gel exhibits a viscosity at yield point of $1 \times 10^9$ to $9 \times 10^9$ mPa·s or $2 \times 10^9$ to $8 \times 10^9$ mPa·s. For example, the gel exhibits a yield stress of $1 \times 10^3$ to $9 \times 10^3$ Pa.

The nanozirconia particles can have a desirable phase. For example, the zirconia nanoparticles are in a tetragonal phase. In another example, 10% or less of the zirconia nanoparticles are in a cubic and/or a monoclinic phase.

In an aspect, the present disclosure provides zirconia green bodies. The zirconia green bodies can be made by removal of water from a formable nanozirconia gel of the present disclosure (e.g., a shaped gel of the present disclosure). The zirconia green bodies can be made by a method of the present disclosure. In an example, a zirconia green body is made by a method of the present disclosure.

The zirconia green body comprises a plurality of zirconia nanoparticles. Suitable zirconia nanoparticles are disclosed herein. For example, the zirconia nanoparticles can be yttria-stabilized YTZP zirconia nanoparticles comprising from 1 to 3 mol % of yttria ($Y_2O_3$). Suitable nanozirconia is commercially available and can be made by methods known in the art. Based on the optical characteristics of the zirconia green bodies, it is considered that the zirconia nanoparticles in a zirconia green body have the same size and size distribution as the nanoparticles of the gel used to make the zirconia green body.

The zirconia nanoparticles in a zirconia green body can have various size distributions. For example, 95% or more of the zirconia nanoparticles by volume have a size of 45 nm or less. In various examples, 96% or more, 97% or more, 98% or more, or 99% of the zirconia nanoparticles by volume have a size of 45 nm or less and/or 99% or more or 99.5% or more of the zirconia nanoparticles by volume have a size of 70 nm or less. In another example, i) 99% of nanoparticles by volume have a size less than 60 nm±10 nm; ii) 95% of nanoparticles by volume have a size less than 40 nm±5 nm; iii) 50% of nanoparticles by volume have a size less than 20 nm±5 nm; and iv.) 5% of nanoparticles by volume have a size less than 12 nm±3 nm.

The zirconia green body is porous. The pores can be interconnected. In various examples, the zirconia green body comprises pores having an average size (e.g., an equivalent average size) of 3 to 10 nm, including all integer nm values therebetween. For example, at least a portion of the pores are interconnected. The pore size/pore size distribution (e.g., average pore size) can be measured by methods known in the art. For example, pore size/size distribution is measured by BET/BJH method using a Quantachrome Nova 1000 surface analyzer.

The zirconia green body can have a range of surface area. In various examples, the zirconia green body has a surface area of 40 to 80 $m^2/g$, including all integer $m^2/g$ values and ranges therebetween. For example, surface area is measured by BET/BJH method using a Quantachrome Nova 1000 surface analyzer.

The zirconia green body can have a range of density. In various examples, the zirconia green body has a density of 50 to 70%%, including all integer % values and ranges therebetween, of the zirconium dioxide theoretical density. In another example, the zirconia green body has a density of 50 to 60% of the zirconium dioxide theoretical density. For example, the theoretical density of tetragonal zirconium dioxide is 6.10 $g/cm^3$. The zirconium theoretical density is dependent on the zirconium dioxide composition (e.g., dopants present in the zirconium dioxide). For example, yttria-doped zirconia has a density of 6.114, 6.106, 6.101, 6.094, or 6.082 $g/cm^3$ for a yttria content of 1.7, 2.0, 2.2, 2.5, or 3.0 mol %, respectively.

The nanozirconia particles can have a desirable phase. For example, the zirconia nanoparticles are in a tetragonal phase. In another example, 10% or less of the zirconia nanoparticles are in a cubic and/or a monoclinic phase.

The zirconia green body can comprise water. In various examples, the zirconia green body further comprises 2 to 5% by weight, including all 0.1% by weight values therebetween, based on the total weight of the zirconia green body (e.g., for a zirconia green body at equilibrium with the ambient environment (e.g., relative humidity of 25 to 75%) at room temperature (e.g., 18 to 25° C.).

The zirconia green body can comprise a processing agent. The zirconia green body can comprise a combination of processing agents. The zirconia green body can have processing agents as described herein. Various amounts of processing agent(s) can be used. In various examples, the amount of the processing agent is 1.5 to 3.3% by weight, including all 0.1% by weight values and ranges therebetween, based on the total weight of the nanoparticles in the zirconia green body. In various example, the amount of the processing agent is 1.7 to 3.1% by weight or 2 to 2.6% by weight, based on the total weight of the nanoparticles in the zirconia green body. In various example, the processing agent comprises (or is) a particle interaction strengthening agent or combination of such agents and the amount of the particle interaction strengthening agent(s) is 0.15 to 1.05% by weight or 0.15 to 0.55% by weight, based on the total weight of the nanoparticles in the zirconia green body. Suitable processing agents are commercially available and can be made by methods known in the art.

The processing agent can be TODA and/or ESD. For example, the processing agent is 2% by weight TODA and/or ESD and 0.1% by weight PEG (e.g., PEG having a molecular weight of 35K (PEG35k)) and 0.05% by weight PVA or 0.5% percent by weight PEG (e.g., PEG having a molecular weight of 35K (PEG35k)) and 0.05% by weight PVA, where the percent by weight values are based on the total weight of the nanoparticles in the zirconia green body.

The processing agent can be covalently bound to the nanozirconia in the zirconia green body. For example, at least a portion of the processing agent is attached via at least one covalent bond to at least a portion of the zirconia nanoparticles in the zirconia green body. For example, the processing agent is attached to a zirconia nanoparticle by one or more nanoparticle surface Zr—O— bond.

The zirconia green body has desirable optical characteristics (e.g., translucency and/or opalescence). For example, where the zirconia green body is translucent and has a transmittance at 560 nm wavelength of 50 to 70% for a 1 to 2 mm thick sample of the zirconia green body and/or the zirconia green body has an opalescence of 20 to 30 for a 1 to 2 mm thick sample of the zirconia green body.

The zirconia green body has desirable physical properties. In various examples, the zirconia green body exhibits a Vickers hardness of 35 to 70 kg/mm$^2$, including all integer kg/mm$^2$ values and ranges therebetween. In various examples, the zirconia green body exhibits a Vickers hardness of greater than 20, 25, 30, 35 or 40 kg/mm$^2$. The Vickers hardness can be measured by methods known in the art. For example, the Vickers hardness is measured by methods described herein (e.g., the method described in Example 29).

The nanozirconia particles of the zirconia green body can have a desirable phase. For example, the zirconia nanoparticles are predominantly, or all, in a tetragonal phase. In another example, 10% or less of the zirconia nanoparticles are in a cubic and/or a monoclinic phase.

The zirconia green bodies can be crack-free. For example, a zirconia green body is free from observable cracks. Cracks can be observed by methods known in the art. For example, cracks can observed visually or by imaging techniques known in the art.

The zirconia green body can have various shapes and/or sizes. In various examples, the zirconia green body has a longest dimension of 15 to 100 mm, including all integer mm values and ranges therebetween. In various examples, the zirconia green body has a dimension of 10 to 30 mm, including all integer mm values and ranges therebetween, in a direction perpendicular to the longest dimension of the zirconia green body (thickness).

In an aspect, the present disclosure provides pre-sintered ceramic bodies. The pre-sintered ceramic bodies can be made from zirconia green bodies of the present disclosure. The pre-sintered ceramic bodies can be made by a method of the present disclosure. In an example, a pre-sintered ceramic body is made by a method of the present disclosure. The pre-sintered ceramic bodies are porous.

The pre-sintered ceramic bodies comprise a plurality of zirconia nanoparticles. The nanoparticles can have a composition as described herein. The zirconia nanoparticles of the pre-sintered ceramic body can have various sizes and size distributions.

The pre-sintered body has desirable optical characteristics (e.g., translucency). In various examples, where pre-sintered body is translucent and has a transmittance at 560 nm wavelength of 40 to 60%, %, including all integer % values and ranges therebetween, for a 1 to 2 mm thick sample of the pre-sintered ceramic body.

The pre-sintered body can have a range of density. In various examples, the pre-sintered body has a density of 50 to 70%, including all integer % values and ranges therebetween, of the zirconium dioxide theoretical density. In another example, the pre-sintered body has a density of 50 to 60% of the zirconium dioxide theoretical density. The theoretical density of zirconium dioxide is as described herein.

The nanozirconia particles of the pre-sintered body can have a desirable phase. For example, the zirconia nanoparticles are in a tetragonal phase. In another example, 10% or less of the zirconia nanoparticles are in a cubic and/or a monoclinic phase.

The pre-sintered bodies can be crack-free. For example, a pre-sintered body is free from observable cracks. Cracks can be observed by methods known in the art. For example, cracks can observed visually or by imaging techniques known in the art.

The pre-sintered body can have various shapes and/or sizes. In various examples, the pre-sintered body has a longest dimension of 15 to 100 mm, including all integer mm values and ranges therebetween. In various examples, the pre-sintered body has a dimension of 10 to 30 mm, including all integer nm values and ranges therebetween, in a direction perpendicular to the longest dimension of the pre-sintered body (thickness).

In an aspect, the present disclosure provides zirconia dental ceramic materials. The zirconia dental ceramic materials can be made from gels of the present disclosure. The zirconia dental ceramic materials can be made by a method of the present disclosure. In an example, a zirconia dental ceramic material is made by a method of the present disclosure.

The zirconia dental ceramic can have at least 95% of all grains by volume have a size of 10 to 300 nm, including all integer nm values and ranges therebetween, and the average grain size is 40 to 150 nm, including all integer nm values and ranges therebetween, and/or the density of the zirconia dental ceramic has a density that is at least 99.5% of zirconium dioxide theoretical density, and/or the zirconia dental ceramic is opalescent. In an example, the average grain size is 80 to 120 nm.

The grain size (e.g., average grain size) can be determined by methods known in the art. For example, the average grain size is determined by ASTM E112 (or EN 623-3). For example, the grain size is determined by imaging methods such as, for example, scanning electron microscopy.

The zirconia dental ceramic materials can be crack-free. For example, a zirconia dental ceramic is free from observable cracks. Cracks can be observed by methods known in the art. For example, cracks can observed visually or by imaging techniques known in the art.

The zirconia dental ceramic has desirable optical characteristics (e.g., translucency and/or opalescence). For example, where the zirconia dental ceramic is translucent and has a transmittance at 560 nm wavelength of 25 to 50% for a 1 to 2 mm thick sample of the zirconia dental ceramic and/or the zirconia dental ceramic has an opalescence of 9 or greater (e.g., 9 to 15) for a 1 to 2 mm thick sample of the zirconia dental ceramic.

The zirconia dental ceramic has desirable physical properties. For example, the zirconia dental ceramic has an average flexural strength of 1200 MPa or greater. In various examples, the zirconia dental ceramic has an average flexural strength of 1500 MPa or greater, 1800 MPa or greater, or 2000 MPa or greater. The average flexural strength can be measured by methods known in the art. For example, the average flexural strength is measured by ISO 6872. For example, the zirconia dental ceramic has an average tensile strength of 500 MPa or greater. The average tensile strength can be measured by methods known in the art. For example, the average tensile strength is measured by ASTM C1273.

In an aspect, the present disclosure provides dental articles. The dental articles can be comprised of zirconia ceramic materials of the present disclosure. The dental articles can be made from pre-sintered bodies of the present disclosure. The dental articles can be made by a method of the present disclosure. In an example, a dental article is made by a method of the present disclosure.

The present disclosure provides various dental articles. For example, the dental article is a blank (e.g., a simple shape) or smart blank (e.g., a shape closer to the final shape of a dental restoration). For example, the dental article is a dental restoration. Examples of dental restorations include, but are not limited to, full-contour FPDs (fixed partial dentures), bridges, implant bridges, multi-unit frameworks, abutments, crowns, partial crowns, veneers, inlays, onlays, orthodontic retainers, space maintainers, tooth replacement appliances, splints, dentures, posts, teeth, jackets, facings, facets, implants, cylinders, and connectors.

In an aspect, the present disclosure provides methods of making gels. The methods are based on the removal of water from an aqueous suspension of zirconia nanoparticles using a semipermeable membrane. The water can be removed without use of an exogenous heat source.

Various aqueous suspensions of zirconia nanoparticles can be used. Examples of suitable zirconia nanoparticles are described herein. For example, aqueous suspensions of yttria-stabilized YTZP zirconia nanoparticles comprising from 1 to 3 mol % of yttria ($Y_2O_3$) were used in this disclosure yielding dental articles with a desirable combination of mechanical and optical properties including strength, translucency and opalescence. In an example, an aqueous suspension comprises zirconia nanoparticles having an average size of 10 to 30 nm and 95% or more of the zirconia nanoparticles by volume have a size of 45 nm or less, where the zirconia nanoparticles are present at less than 70% by weight based on the total weight of the aqueous suspension. In various examples, the zirconia nanoparticles are present at 50 to 70% by weight of the aqueous suspension or 50 to 60% by weight of the aqueous suspension.

In an example, aqueous suspensions were modified with processing agents and attrition milled before the osmotic processing, as described in details in Comparative Example 1 and Example 7. For example, 2-[2-(2-methoxyethoxy) ethoxy] acetic acid (also known as 3,6,9-trioxadecanoic acid abbreviated as TODA and TODS) and ESD, were added at 2% by weight based on total weight of the suspension to the zirconia solid content in the suspension. The suspensions were named as 2TODA suspension and 2ESD suspension respectively. Both processing agents stabilized the suspensions concentrated to a loading of 55% by weight based on total weight of the nanoparticles in the suspension to facilitate attrition milling process.

Advantages of using TODA combined with the appropriate capping step are considered to be as follows: TODA molecules, with a tail of hydrophilic multi-ether group and a head of carboxylic acid group, can be chemically bonded onto the zirconia nanoparticle surfaces by reacting with the surface hydroxyl groups. The multi-ether tails provide stearic repulsion needed to keep zirconia nanoparticles well dispersed in water and prevent agglomeration when suspension is concentrated. Compared to ionic processing agents, such as ionic amines like tetramethylammonium hydroxide (TMAH), polyacrylates salts like ammonium polyacrylate, or other commonly used anionic processing agents like triammonium citrate (TAC), which are physically absorbed on nanoparticulate surfaces, the chemically bonded TODA dispersant is better suited to survive the osmotic processing of this disclosure without detaching from the nanoparticle surfaces and escaping through the dialysis membrane tubing into osmotic solution outside membrane. Furthermore, since TODA is acidic, it shifts the pH value of the suspension to lower values away from its isoelectric point (IEP). On the other hand, adding processing agents such as TMAH and TAC can potentially cause the irreversible agglomeration of particles since they shift the pH to basic range on the other side of IEP casing gelation often associated with formation of hard agglomerates. It was also found that gels made from 2TODA suspensions have higher green body survival rate than 2ESD suspensions when no particle interaction strengthening agent (e.g., polymeric processing agent) was added. It was unexpectedly found that with proper capping procedure the amount of TODA needed to provide well dispersed suspension was well below saturation limit required to cover the whole surface of all the nanoparticles in suspension (see FIG. 4).

Any steric, electrosteric or electrostatic processing agent, for example, 2-[2-(2-methoxyethoxy)ethoxy] acetic acid (TODA), 2-(2-methoxyethoxy) acetic acid (also known as 3,6-dioxaheptanoic acid abbreviated as DOHA) or ESD, can be used as long as it allows production and use (according to examples of this disclosure) of well-dispersed suspensions and gels at such agent concentrations not exceeding 2.2% by weight based on total weight of the nanoparticles in the suspension and providing that such dispersant is not increasing pH of the starting nanozirconia suspension to above 5.5 and, for example, not higher than 4.5.

In an example, a method of making a gel of the present disclosure (e.g., a gel of Statement 1) comprises: a) providing an aqueous suspension comprising zirconia nanoparticles having an average size of 10 to 30 nm and 95% or more of the zirconia nanoparticles by volume have a size of 45 nm or less, where the zirconia nanoparticles are present at less than 70% by weight of the aqueous suspension; and b) concentrating the aqueous suspension by removing water from the aqueous suspension with a semipermeable membrane, where the water removal is driven by intrinsically induced pressure or externally imposed pressure, until the suspension has zirconia nanoparticles present at 70 to 85% by weight of the aqueous suspension, whereby the gel is formed. In various examples, the zirconia nanoparticles are present at 50 to 70% by weight of the aqueous suspension or 50 to 60% by weight of the aqueous suspension.

The aqueous suspension can further comprise a processing agent. The aqueous suspension can comprise varying amounts of one or more processing agents. Unless otherwise indicated, the amount of processing agent(s) in the aqueous suspension is a percentage by weight based on the total weight of the nanoparticles in an aqueous suspension. In various examples, the total amount of the processing agents is present at 1.5% to 3.3% by weight, including all 0.1% by weight values and ranges therebetween, based on the total weight of the nanoparticles in the aqueous suspension. Examples of aqueous suspensions comprising an electrostatic colloid stabilizers are referred to herein as a 2ESD or 2ESD suspension. At least a portion or all of the processing agent(s) is/are attached via at least one covalent bond to at least a portion of the zirconia nanoparticles.

A method of making a gel can comprise attrition milling a starting aqueous suspension. A method of making a gel can comprise attrition milling a starting aqueous suspension and subjecting the attrition milled starting aqueous suspension to centrifugation.

Figure 6A:
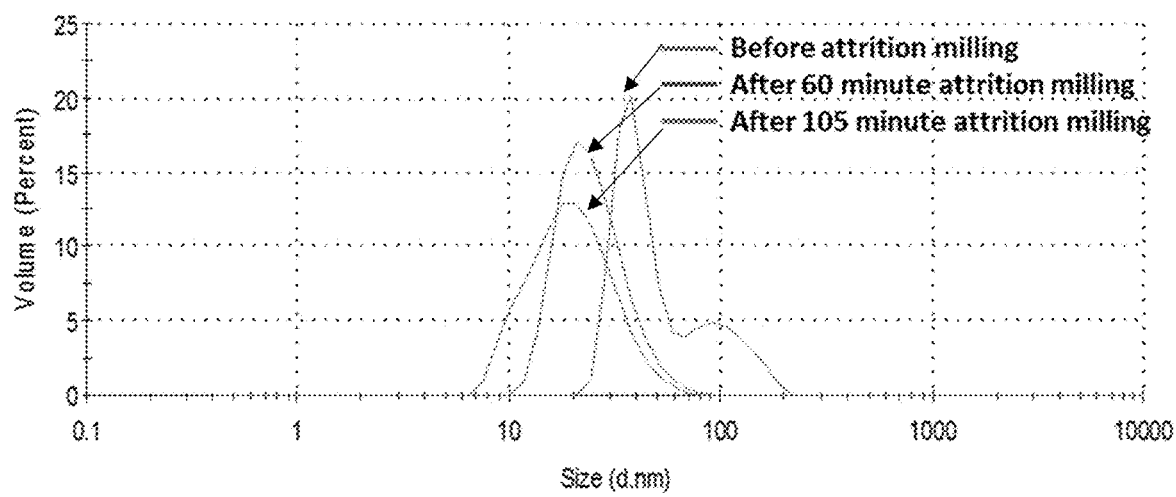
FIGS. 6A and 6B. DLS measurement of volume size distribution of A) an example of a 2TODA suspension, and B) an example of a 2ESD suspension during attrition milling, indicating the deagglomeration of zirconia nanoparticles.
Figure 6B:
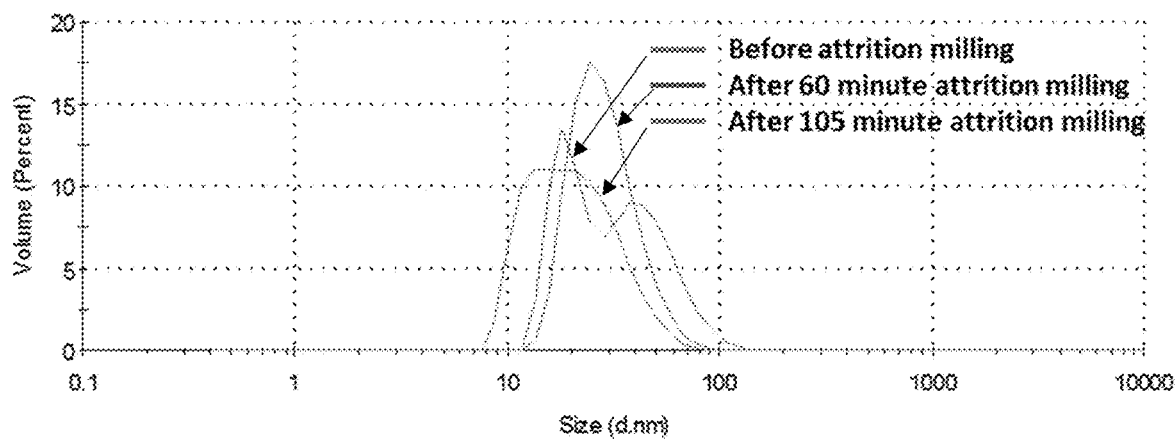

Deagglomeration occurs during the attrition milling process, as evidenced by, for example, a drop of viscosity and arising translucency of the suspension. For example, as described in Comparative Example 1, the viscosity of the 2TODA suspension was typically 50-60 cP before attrition milling and fell to 10 to 20 cP after 105 minute attrition milling at the same shear rate of 2.64 s−1. The milky suspension started to turn translucent after relatively short attrition milling time. After 30 minutes the milled suspension became very noticeably translucent and translucency kept increasing until reaching maximum at about 105 minutes of attrition milling. The deagglomeration of particles can also be directly observed by Dynamic Light Scattering (DLS) measurements as shown in FIG. 6B. Before attrition milling both suspensions had unimodal or bimodal particle size distribution with the volume average particle size ranging from 54 to 68 nm for 2TODA suspensions and 36 to 44 nm for 2ESD suspensions. After 105 minutes of attrition milling, the larger peak disappeared if present initially and volume average particle size for both suspensions decreased to 18 to 25 nm range. The attrition milling step is very important to form an agglomeration-free gel, without which the formed gel by osmotic processing was opaque even at a loading less than 70% by weight based on total weight of the suspension.

Figure 13:
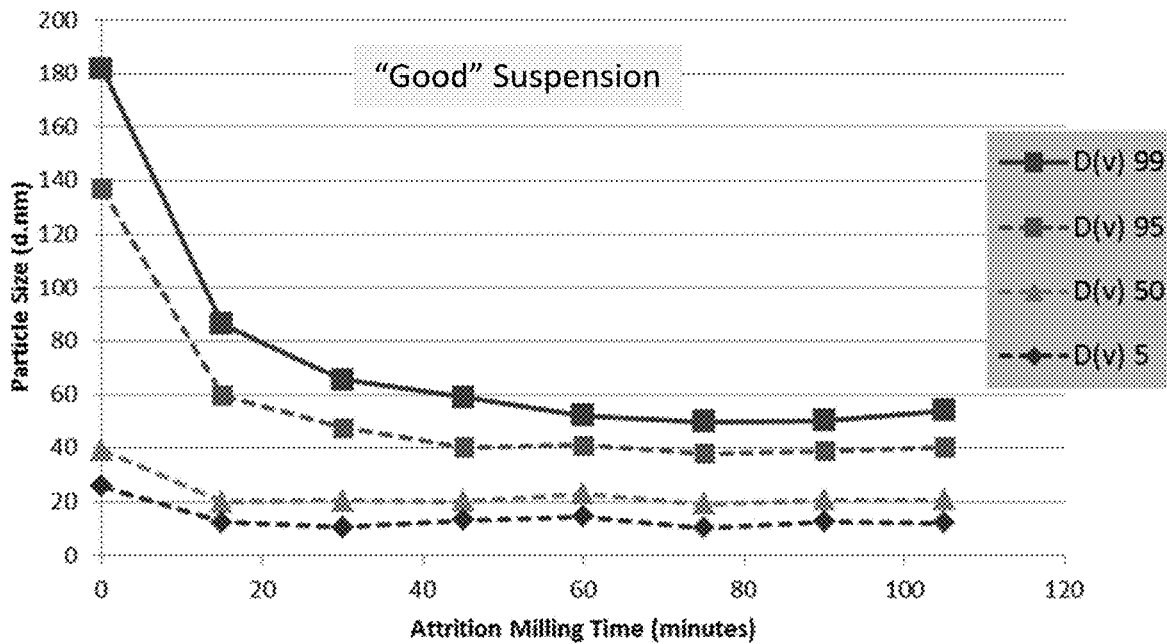
FIG. 13. Example of particle size by volume percentage versus attrition milling time.
Figure 13:
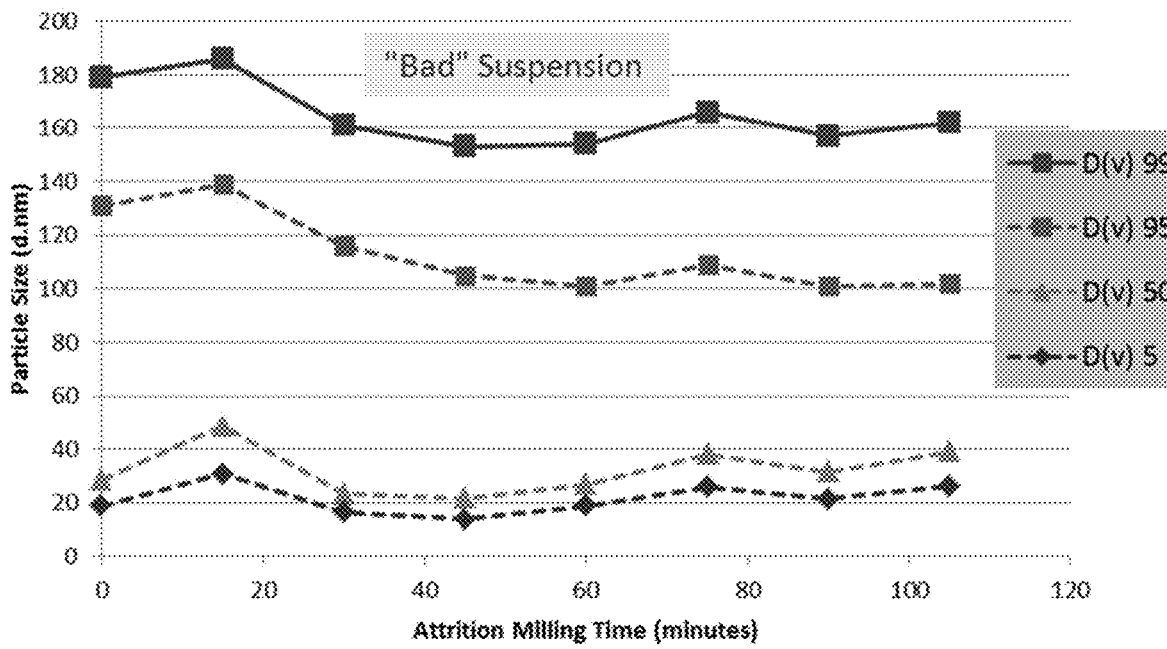

The most indicative parameter to evaluate the quality of suspension is particle size distribution by volume weight (volume percentage). For example, the expression of D(v) 50=100 nm means that 50 vol % of particles are smaller than 100 nm. For example, FIG. 13 shows that the attrition milling effectively reduced the particle size for "good" suspensions after 105 minutes. Attrition milling specifically targets to break large agglomerates. However, for "bad" suspensions, attrition milling was not able to reduce particle size or break large agglomerates.

For example, a method of making a gel can comprises attrition milling a starting aqueous suspension comprising zirconia nanoparticles having an average size greater than 50 nm, where the zirconia nanoparticles are present at 50% or greater by weight of the starting aqueous suspension, and, optionally, subjecting the attrition milled starting aqueous suspension to centrifugation, to provide an aqueous suspension (e.g., an aqueous suspension of a) above).

A starting aqueous suspension can comprise zirconia nanoparticles having an average size greater than 50 nm, where the zirconia nanoparticles are present at less than 50% by weight of the starting aqueous suspension based on the total weight of the starting aqueous suspension. In this case a method further comprises: i) concentrating the starting aqueous suspension by heating and/or applying sub-ambient pressure to the starting aqueous solution until the zirconia nanoparticles are present at 50% or greater by weight; and ii) attrition milling the concentrated starting aqueous suspension from i) and, optionally, subjecting the attrition milled starting aqueous suspension to centrifugation, to provide the aqueous suspension of a).

A colloidal stabilizer can be added to the starting aqueous suspension prior to attrition milling. For example, the starting aqueous suspension prior to attrition milling further comprises a colloidal stabilizer (e.g., the total amount of the colloidal stabilizer is present at 0.5 to 2.5% by weight based on the total weight of zirconia nanoparticles in the starting aqueous suspension.

A particle interaction strengthening agent can be added to the starting aqueous suspension after attrition milling. For example, a particle interaction strengthening agent is added to the starting aqueous suspension after attrition milling (e.g., the particle interaction strengthening agent is present at 0.1 to 1.5% by weight based on the total weight of the nanoparticles in the milled starting aqueous suspension).

The aqueous suspension can have various pH values. In an example, the pH of the aqueous suspension is 2.5 to 5.5, including all 0.1 pH values and ranges therebetween. In an example, the pH of the aqueous suspension is 2.5 to 4.5. In various examples, the pH of the aqueous suspension is 5.5 or less or 4.5 or less.

Water can be removed from the aqueous suspension using an intrinsically induced pressure. Without intending to be bound by any particular theory, it is considered that intrinsically induced pressure results from a thermodynamic driving force or a difference in chemical potential (e.g., resulting from different solute concentrations of two solutions on opposite sides of a semipermeable membrane).

The water removal process (e.g., a portion of or all of the process) can be carried out with physical agitation (e.g., shaking or stirring) of the aqueous suspension. For example, the aqueous suspension is physically agitated during at least a portion of or all of the water removal process. Without intending to be bound by any particular theory, it is considered that physical agitation during water removal homogenizes the resulting gel. It is desirable the physical agitation result in minimal or no cavitation (e.g., no observable cavitation) of the aqueous suspension. For example, during a portion of or all of the water removal (e.g., water removal by osmosis) the aqueous suspension is shaken. It is desirable the physical agitation on the aqueous suspension (not just the osmotic solution) can significant improve the homogeneity and cause very minimal cavitation of the suspension as it is concentrated to form the gel.

Water can be removed from the aqueous suspension using an osmotic process. An osmotic process provides intrinsically induced pressure. For example, the concentrating in a method is carried out by an osmotic process.

FIG. 5 is a diagram of an example of osmotic processing, which is described in detail in Example 1. Nanozirconia suspensions with 55 wt % solid loading (based on total weight of the nanoparticles in the suspension) were loaded in a semi-permeable membrane tubing, while leaving ⅓ to ¼ of the tubing unfilled. The loaded tubing was then closed and immersed in a polymer/water osmotic solution in a closed container. The molecular weight of the polymer was chosen to be greater than the molecular weight cut off (MWCO) of the membrane so that the polymer molecules could not penetrate the membrane to contaminate the suspension. The container was then placed on a shaking table and subjected to continuous agitation for 16 to 36 hours at 100 to 150 rpm. It is important to keep the tubing not fully filled and keep it continuously agitated, so that the suspension tumbles in the tubing and is homogenized during the process. Driven by the osmotic pressure, water was drawn from the nanoparticle suspension inside the semi-permeable tubing to the osmotic solution outside, while zirconia nanoparticles could not pass through due to their bigger size. The suspension was thus concentrated and later formed a gel. It is evidenced that the osmotic processing did not result in the agglomeration of zirconia nanoparticles since the gel was highly translucent and could be totally re-dispersed in water to form a stable and translucent suspension. The formed gel needs to be soft, homogenous and easily deformable so that it can be shaped by various kinds of forming methods such as centrifugal casting, CIP, vibra-forming, etc.

The osmotic solution used in the osmotic process can be an aqueous polymer solution. Various polymers that are soluble in an aqueous medium (e.g., water) can be used. For example, the polymer of the aqueous polymer solution is selected from the group consisting of polyethylene glycol (PEG), poly-ethylene-co-propylene glycol, polyethylene imine (PEI), and combinations thereof.

For example, the osmotic process comprises: a) placing the aqueous suspension comprising zirconia nanoparticles in an enclosure at least a portion of an external surface of which is a semipermeable membrane; b) contacting the enclosure with an osmotic solution such that the osmotic solution and the aqueous suspension are in fluid contact; c) agitating the aqueous suspension; and d) optionally, heating the osmotic solution.

Water can be removed from the aqueous suspension using a tangential flow filtration process. In this case, the water removal is driven by externally imposed pressure. For example, the concentrating in a method is carried out using a tangential flow filtration process.

For example, the tangential flow filtration process comprises: a) flowing the aqueous suspension comprising zirconia nanoparticles through a channel at least a portion an external surface of which is the semipermeable membrane; b) repeating a) until the a desired amount of water is removed from the aqueous suspension comprising zirconia nanoparticles; and c) optionally, heating the aqueous suspension comprising zirconia nanoparticles.

The semipermeable membrane in the tangential flow filtration process can be contacted with an osmotic solution. The osmotic solution can be an osmotic solution described herein.

Externally imposed pressure can be provided by mechanical means. For example, externally imposed pressure can be provided by a pump (e.g., a mechanical pump). In various examples, an externally imposed pressure of 5 to 200 psi, including all integer psi values and ranges therebetween.

In an aspect, the present disclosure provides methods of making zirconia green bodies. The methods are based on the removal of water (e.g., non-equilibrium water) from a gel (e.g., a gel that has been shaped into a desired shape).

For example, a method of forming a green body of the present disclosure (e.g., a green body of Statement 22) comprises: a) providing a gel of the present disclosure (e.g., a gel of Statement 1); b) shaping the gel into a desired shape; and c) removing water from the shaped gel, whereby the zirconia green body having 2% to 5% water, including all 0.1% values and ranges therebetween, based on the weight of the zirconia green body is formed.

The gel can be shaped. For example, the shaping of the gel comprises shaping the gel into an isotropically enlarged, uniform shape. The shaping can be carried out using centrifugal casting, cold isostatic pressing (CIP), vibra forming, or injection molding.

Centrifugal casting and cold isostatic pressing (CIP) can be used to form desired shapes from gels, for example, as described in Example 1 and Example 13, respectively. In order to form a green body to survive the drying process, it is desirable that the shaped gel has minimum amount of defects (bubbles, voids and surface roughness, etc.). Gel formability ranking is thus introduced as a qualitative measure of the given gel capacity to form such shapes, which is largely determined by the gel yield stress and viscosity.

Figure 7A:
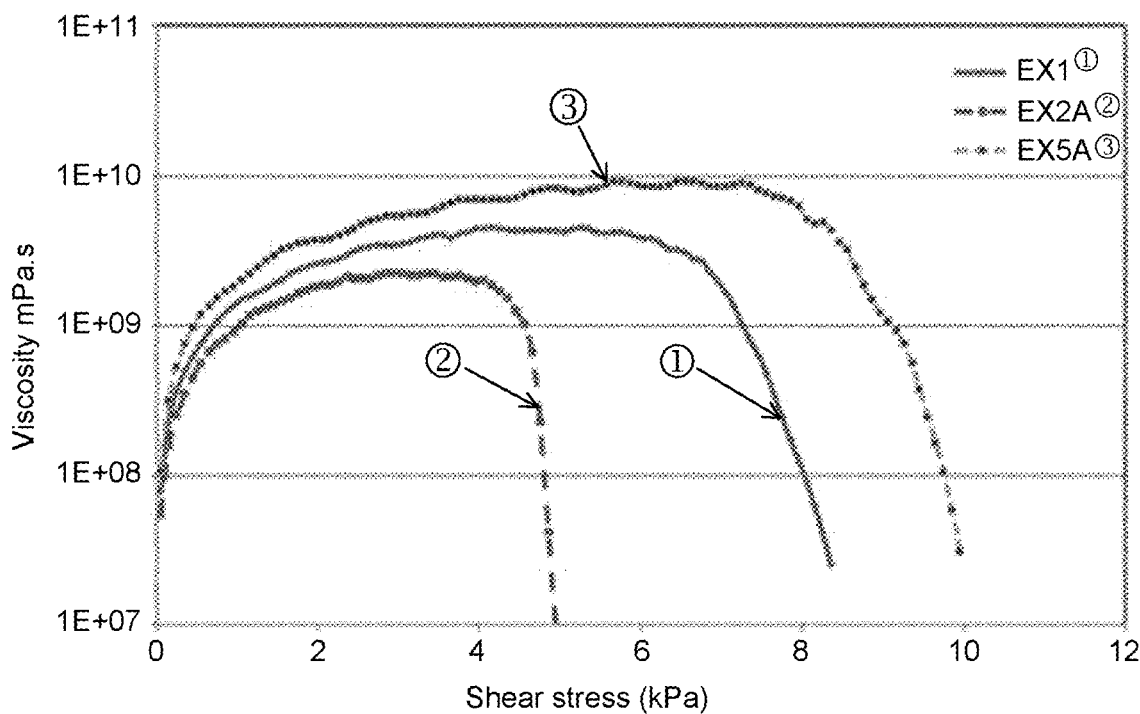
FIGS. 7A and 7B. Gel viscosity vs. shear stress of A) 2TODA gel samples (Example 1, 2A and 5A), and B) 2ESD gel samples (Example 23, 8A and 11A).
Figure 7B:
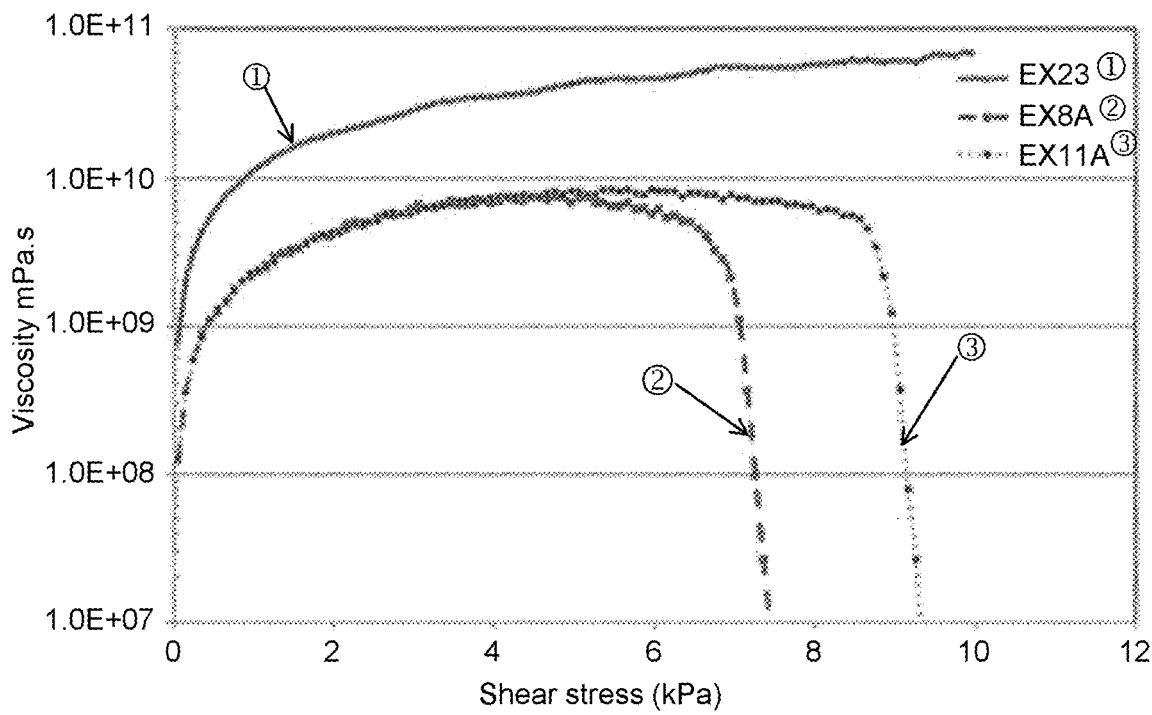
Figure 8A:
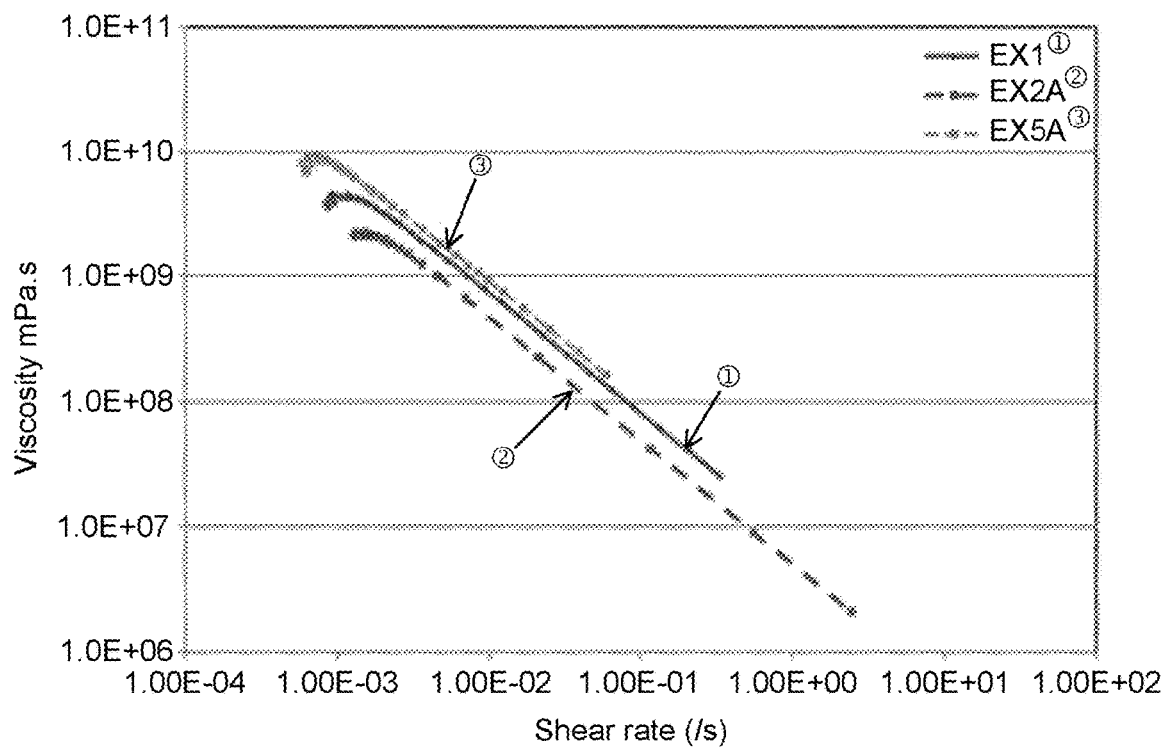
FIGS. 8A and 8B. Gel viscosity vs. shear rate, after yield point, of A) 2TODA gel samples (Example 1, 2A and 5A), and B) 2ESD gel samples (Example 23, 8A and 11A).
Figure 8B:
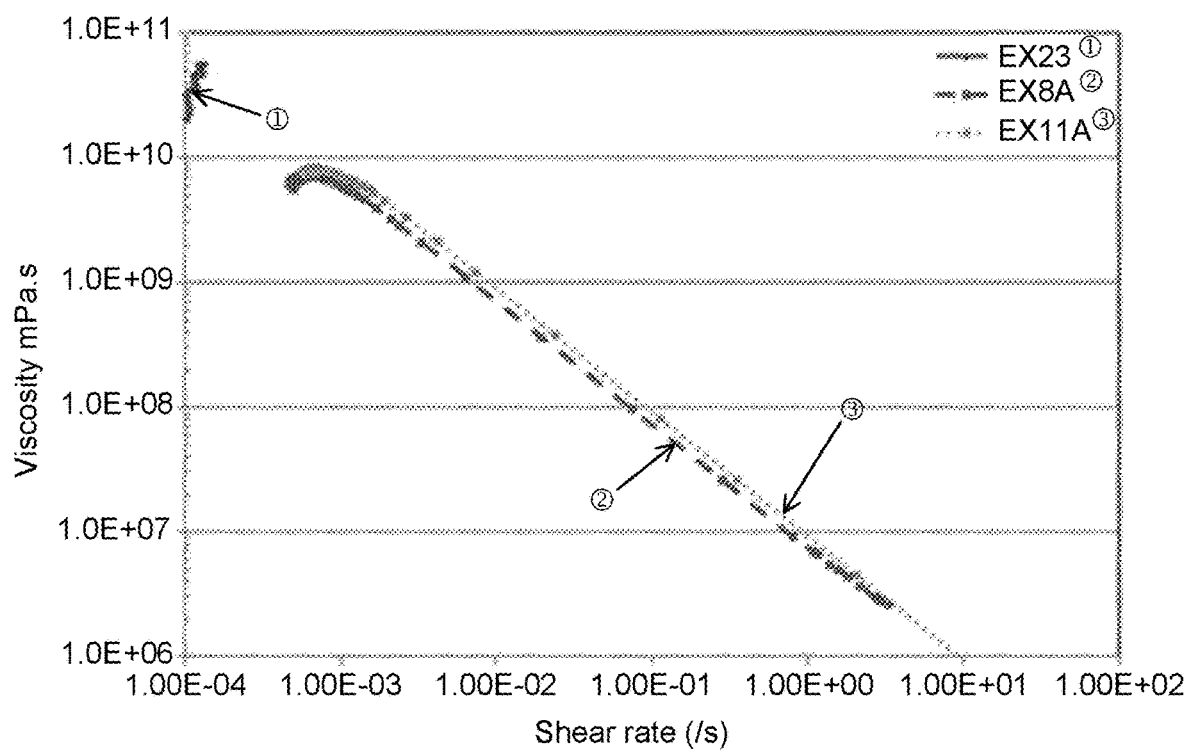
Figure 9:
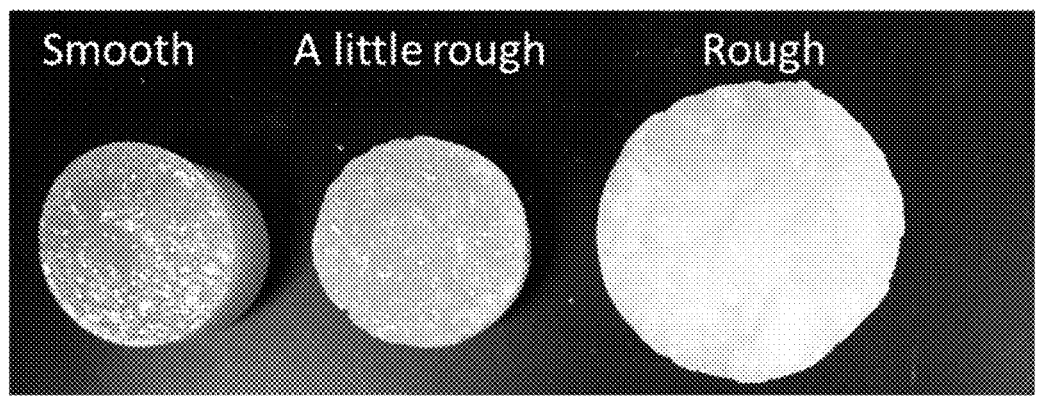
FIG. 9. Top surface smoothness/roughness of examples of centrifugal-cast blanks.

Gel yield stress and viscosity were characterized by rheometry measurements and correlated with its formability ranking, which is described in Example 28. Both gels made from 2TODA suspensions (Example 1, 2A and 5A) and gels made from 2ESD suspensions (Example 23, 8A and 11A) were measured. It was found that the gels, except for gel of Example 23, were initially deformed like an elastomer until a yield stress was reached. Further increasing shear stress results in the flow behavior of the gels, as shown in FIGS. 7A and 7B. The gel of Example 23 is too rigid to yield even at the maximum shear stress of 10,000 Pa. When shear stress exceeded the yield stress, gels showed a strong shear-thinning behavior as shown in FIGS. 8A and 8B. These measurement results were summarized in Table 1A, where the assignment of softness/rigidity, ranging from very soft, soft, semi-soft, semi-rigid to rigid, was also listed. Based on these experimental results, a qualitative assessment of gel formability ranking was established based on the gel viscosity at yield point, as shown in Table 1B. Gels with viscosity less than $4 \times 10^9$ mPa·s are assigned to be the most formable (Level 5), while gels with viscosity of 4 to $8 \times 10^9$ mPa·s and 8 to $12 \times 10^9$ mPa·s are also formable but with lower formability levels (Level 3-4 and 1-2 respectively). The higher the gel formability level, the less likely that bubble/voids would be trapped in the body when they are formed. Furthermore, the top surface of the formed body is smoother when the gel formability is higher, as shown in FIG. 9 where centrifugal casting was used.

TABLE 1A

Viscosity and yield stress measured with Kinexus Ultra+ Rotational Rheometer by Malvern (Example 28)

| Gel | Processing agent | Gel loading, wt % (vol %) | Yield stress, $\times 10^3$ Pa | Viscosity at yield point ($\times 10^9$ mPa·s) | Softness/Rigidity |
|---|---|---|---|---|---|
| gel of EX1 | 2TODA | 81.3 (41.6) | 4.1 | 4.6 | soft |
| gel of EX2A | 1% PEG35K | 77.4 (36.0) | 3.0 | 2.2 | very soft |
| gel of EX5A | 0.1% PEG35K + 0.05% PVA | 78.8 (37.9) | 6.6 | 9.3 | semi-soft |
| gel of EX23 | 2ESD | 80.2 (39.9) | >10 | >46.3 | semi-rigid to rigid |
| gel of EX8A | 1% PEG35K | 75.8 (33.9) | 5.1 | 8.7 | soft to semi-soft |
| gel of EX11A | 0.1% PEG35K + 0.05% PVA | 75.3 (33.3) | 5.2 | 8.7 | soft to semi-soft |

TABLE 1B

Gel softness/rigidity and formability correlation to gel viscosity at yield point

| Softness/Rigidity* | Formability | Viscosity at yield point, $\times 10^9$ mPa·s |
|---|---|---|
| Very soft | Level 5: Best formability with smooth top surface and the least likelihood of trapped bubbles | <4 |

TABLE 1B-continued

Gel softness/rigidity and formability correlation to gel viscosity at yield point

| Softness/Rigidity* | Formability | Viscosity at yield point, × $10^9$ mPa·s |
|---|---|---|
| Soft | Level 3-4: Formable but top surface could be a little rough | 4-8 |
| Semi-soft | Level 1-2: Formable with rough top surface, bubbles more likely trapped | 8-12 |
| Semi-rigid | Level 0: Not soft enough (too hard) to be formable | 12-50 |
| Rigid | Semi solid to solid | >50 |

1 mPa·s = 1 cP = 0.01 P = 0.001 Pa·s

A semi-rigid gel (viscosity 12 to 50×$10^9$ mPa·s) or rigid gel (viscosity greater than 50×$10^9$ mPa·s) are considered to be non-formable. These gels are either not soft enough to form a shape with the above-mentioned forming methods, or just too solid (not plastic, stiff, i.e., rigid) to even deform.

The solid loading of the gel is a significant major factor affecting gel formability and can be controlled by osmotic time. However, other factors, such as the type of processing agent(s) added in the suspension, can also have a significant impact on formability.

The water can be removed by holding a gel (e.g., a shaped gel) in a controlled-humidity and controlled-temperature environment. In various examples, the humidity of the controlled-humidity environment is 10 to 90%, including all integer % values and ranges therebetween, and the temperature is 20 to 50° C., including all integer ° C. values and ranges therebetween.

The water can be removed by holding a gel (e.g., a shaped gel) in multiple controlled-humidity and controlled-temperature environments having different humidity and temperature. For example, the removing is carried out by holding the shaped gel in two or more different controlled-humidity environments, where the humidity in each of the individual environments is 10 to 90% and different than the other individual environments and is decreased relative to the previous environment in which the gel was held. For example, a first environment has a humidity of 70 to 90% and a second environment has a humidity of 10 to 30%.

For example, the removing is carried out by: i) holding the shaped gel in the first environment for 1 to 10 days (e.g., 1, 2, 3, 4, 5, 6, 7, 8, 9, or 10 days, or any 0.1 day value between 1 and 10 days; and ii) subsequently holding the shaped gel from i) in two or more other environments for 1 to 10 days, where the humidity in each of the other environments is from 30 to 90% and is decreased relative to the previous environment in which the gel was held and the last environment has a humidity of 10 to 30%.

In an aspect, the present disclosure provides methods of making pre-sintered ceramic bodies. The methods are based on heating a zirconia green body to remove organic materials from the zirconia green bodies.

For example, burning out of organics of green bodies of this disclosure can be carried out at the rates from, for example, 0.1° C./min to 10° C./min and temperatures from 500° C. to 800° C. with or without short or long isothermal holds at the temperatures associated with mass loss and/or exothermic activity. Typically slower heating rates may help to eliminate at least some of the isothermal holds while faster heating rates may require a few isothermal holds at the temperatures associated with mass loss and/or exothermic activity including low temperature isothermal holds (less than 150° C.) for elimination of the absorbed water. Pre-sintering can be carried out concurrently or separately from organic burn out, in one or multiple separate heating cycles carried out in one or different furnaces including environmental chambers, vacuum furnaces or furnaces able to operate at partial pressures. In cases when removal of organics is overlapping with pre-sintering, which is more noticeable at higher starting green densities and finer nanoparticle sizes wherein organics burn-out and shrinkage due to interparticle necking cannot be easily deconvoluted, the resulting "pre-sintered brown" bodies are still called brown bodies despite their noticeable shrinkage. The latter can happen when green density is above 55% of theoretical density, and average particle size in the starting nanozirconia green body is less than 25 nm; and organic burn out is carried to the temperatures higher than 550° C. Organic burn out of commercially relevant size blanks (greater than 10 mm in thickness) and large green-milled restorations is done much slower than small samples but once organics (e.g., processing agents) are fully removed pre-sintering and sintering to full density can be carried out at rates higher than 10° C./min.

A pre-sintered ceramic body (e.g., a pre-sintered ceramic body of Statement 44) can be made by heating a zirconia green body of the present disclosure (e.g., a zirconia green body of Statement 22) at a temperature of 400 to 1000° C., including all integer ° C. values and ranges therebetween. The heating can be carried out at a heating rate of 0.1 to 10° C./min, including all 0.1° C./min values and ranges therebetween. For example, a method of making a pre-sintered ceramic body of the present disclosure (e.g., a pre-sintered ceramic body of Statement 44), comprises heating a zirconia green body of the present disclosure (e.g., a zirconia green body of Statement 22) at a temperature of 400 to 1000° C., where the zirconia green body may be heated at a rate of 0.1 to 10° C./min.

In an aspect, the present disclosure provides methods of making zirconia dental ceramics. The methods are based on heating a pre-sintered ceramic body as described herein. In various examples, a method of making a zirconia dental ceramic material comprises heating a pre-sintered ceramic body as described herein.

In an aspect, the present disclosure provides methods of making dental articles. The methods are based on shaping and heating a pre-sintered ceramic body or zirconia green body.

A dental article of the present disclosure (e.g., a dental article of Statement 55) can be made by first shaping comprising shaping a green body of the present disclosure (e.g., a green body of Statement 22) or a pre-sintered ceramic body of the present disclosure (e.g., a pre-sintered ceramic body of Statement 44). The shaping can be carried out by methods known in the art. For example, the shaping is carried out by CAD/CAM, Low Pressure Injection Molding (LPIM), or dental heat pressing. Then the shaped green body or shaped pre-sintered ceramic body is heated at a temperature of 1000 to 1200° C., to form the dental restoration.

For example, a method of making a dental article of the present disclosure (e.g., a dental article of Statement 55) comprises shaping (e.g., by CAD/CAM, LPIM, or dental heat pressing) a green body of the present disclosure (e.g., a green body of Statement 22) or a pre-sintered ceramic body of the present disclosure (e.g., a pre-sintered ceramic body of Statement 44) and heating the shaped green body or shaped pre-sintered ceramic body at a temperature of 1000 to 1200° C., whereby the dental restoration is formed. For example, the shaping of a zirconia green body of the present disclosure (e.g., a zirconia green body of Statement 22) or a pre-sintered ceramic body of the present disclosure (e.g. a pre-sintered ceramic body of Statement 44) is carried out using CAD/CAM, LPIM, or dental heat pressing.

The steps of the methods described in the various embodiments and examples disclosed herein are sufficient to produce materials of present disclosure (e.g., gels, zirconia green bodies, pre-sintered ceramic bodies, zirconia ceramics, and dental restorations) of the present disclosure. Thus, in an embodiment, a particular method consists essentially of a combination of the steps of the method disclosed herein. In another embodiment, a particular method consists of such steps.

In the following Statements, various examples of the compositions and methods of the present disclosure are described:

Statement 1. A gel comprising a plurality of zirconia nanoparticles and water, where the zirconia nanoparticles have an average size of 10 to 30 nm, 95% or more of the zirconia nanoparticles by volume have a size of 45 nm or less, and the gel is a formable gel (e.g., formable into the desired shape (e.g., by centrifugal force, vibration, pressure, or a combination thereof) and capable of losing water in a controlled-humidity and controlled-temperature environment without cracking while maintaining the shape integrity, whereby a zirconia green body having 2% to 5% water based on the weight of the zirconia green body is formed).

Statement 2. A gel according to Statement 1, where: i) 99% of nanoparticles by volume have a size less than 60 nm±10 nm; ii) 95% of nanoparticles by volume have a size less than 40 nm±5 nm; iii) 50% of nanoparticles by volume have a size less than 20 nm±5 nm; and iv.) 5% of nanoparticles by volume have a size less than 12 nm±3 nm.

Statement 3. A gel according to any one of Statements 1 and/or 2, where 95% or greater by volume of the zirconia nanoparticles comprise 1 to 5 crystallites.

Statement 4. A gel according to any one or more of the preceding Statements, where the zirconia nanoparticles are present at 70 to 85% by weight based on the total weight of the gel.

Statement 5. A gel according to any one or more of Statements 1 to 4, where the zirconia nanoparticles are present at 28 to 48% by volume based on the total volume of the gel.

Statement 6. A gel according to any one or more of the preceding Statements, where the gel further comprises one or more processing agents and/or one or more additives (e.g., oxides and colorants (e.g., coloring oxides and coloring ions), compounds comprising rare earth elements and/or comprising lanthanum group elements, and combinations thereof).

Statement 7. A gel of Statement 6, where the processing agent is selected from the group consisting of colloid stabilizers, particle interaction strengthening agents, and combinations thereof.

Statement 8. A gel of Statement 7, where the particle interaction strengthening agent is selected from the group consisting of polyethylene glycol (PEG), polyethylene oxide (PEO), polyvinylalcohol (PVA), methyl cellulose, polyacrylic acid, dextrin, poly-ethylene-co-propylene-glycol, and combinations thereof.

Statement 9. A gel of Statement 7, where the colloid stabilizers are selected from dispersants, protective colloids, and combinations thereof.

Statement 10. A gel of Statement 7, where the colloid stabilizer is selected from the group consisting of organo-carboxylic acids (e.g., polyoxocarboxylic acids such as, for example, $CH_3-[O-(CH_2CH_2)]_xCO_2H$ and salts thereof, where x is 1 to 120, 1 to 50, or 1 to 30) and salts thereof, amino acids and salts thereof, organoamines and ammonium salts thereof, organoalcohols and organosilanes.

Statement 11. A gel of Statement 10, where the colloid stabilizers are selected from the group consisting of 2-[2-(2-methoxyethoxy)ethoxy]acetic acid (TODA), 2-(2-methoxyethoxy)acetic acid (DOHA), O-(2-carboxyethyl)-O'-methyl-undecaethylene glycol, methoxypolyethylene glycol propionic acid (e.g., having a molecular weight of 5,000), 3,6,9-trioxaundecanedioic acid, polyacrylic acid, bicine, dodecyl amine, tetradecyl methyl amine, cetyl trimethyl ammonium bromide (CTAB), ammonium polyacrylate, polyethylene glycol dodecyl ether, trimethoxy(propyl) silane, 2-[(acetoxy(polyethyleneoxy)propyl]triethoxysilane and 2-[methoxy(triethyleneoxy)propyl]trimethoxysilane, and combinations thereof.

Statement 12. A gel of Statement 6, where the processing agent is 2% by weight TODA and/or ESD and 0.1% by weight PEG35K and 0.05% by weight PVA or 0.5% percent by weight PEG35k and 0.05% by weight PVA, where the percent by weight values are based on the total weight of the nanoparticles in the gel.

Statement 13. A gel according to any one or more of Statements 6 to 11, where the amount of the processing agent is 1.5 to 3.3% by weight based on the total weight of the nanoparticles in the gel.

Statement 14. A gel according to any one or more of Statements 6 to 13, where at least a portion of the processing agent is attached via at least one covalent bond to at least a portion of the zirconia nanoparticles.

Statement 15. A gel according to any one or more of the preceding Statements, where the gel is translucent and has a transmittance at 560 nm wavelength of 60 to 80% for a 1 to 2 mm thick sample of the gel.

Statement 16. A gel according to any one or more of the preceding Statements, where the gel has an opalescence of 20 to 30 for a 1 to 2 mm thick sample of the gel.

Statement 17. A gel according to any one of the preceding Statements, where the gel is redispersible in an aqueous medium.

Statement 18. A gel according to any one or more of the preceding Statements, where the gel exhibits a viscosity at yield point of $1 \times 10^9$ to $12 \times 10^9$ mPa·s.

Statement 19. A gel according to any one or more of the preceding Statements, where the gel exhibits a yield stress of $1 \times 10^3$ to $9 \times 10^3$ Pa.

Statement 20. A gel according to any one or more of the preceding Statements, where in the zirconia nanoparticles are in a tetragonal phase.

Statement 21. A gel according to any one or more of Statements 1 to 19, where 10% or less of the zirconia nanoparticles are in a cubic and/or a monoclinic phase.

Statement 22. A zirconia green body comprising a plurality of zirconia nanoparticles, where the zirconia nanoparticles have an average size of 10 to 30 nm and 95% or more of the zirconia nanoparticles by volume have a size of 45 nm or less.

Statement 23. A zirconia green body, of Statement 22, where: i) 99% of nanoparticles by volume have a size less than 60 nm±10 nm; ii) 95% of nanoparticles by volume have a size less than 40 nm±5 nm; iii) 50% of nanoparticles by volume have a size less than 20 nm±5 nm; and iv.) 5% of nanoparticles by volume have a size less than 12 nm±3 nm.

Statement 24. A zirconia green body according to any one or more of Statements 22 to 24, where the zirconia green body is porous.

Statement 25. A zirconia green body of Statement 24, where the zirconia green body comprises pores having a size of 3 to 10 nm and at least a portion of the pores are interconnected.

Statement 26. A zirconia green body according to any one or more of Statements 22 to 25, where the zirconia green body has a surface area of 40 to 80 m$^2$/g.

Statement 27. A zirconia green body according to any one or more of Statements 22 to 26, where the zirconia green body has a density of 50 to 70% of the zirconium dioxide theoretical density.

Statement 28. A zirconia green body according to any one or more of Statements 22 to 27, where in the zirconia nanoparticles are in a tetragonal phase.

Statement 29. A zirconia green body according to any one or more of Statements 22 to 27, where 10% or less of the zirconia nanoparticles are in a cubic and/or a monoclinic phase.

Statement 30. A zirconia green body according to any one or more of Statements 22 to 29, where the zirconia green body further comprises 2 to 5% by weight based on the total weight of the zirconia green body at equilibrium with the ambient environment at room temperature.

Statement 31. A zirconia green body according to any one or more of Statements 22 to 30, where the zirconia green body further comprises a processing agent.

Statement 32. A zirconia green body of Statement 31, where the processing agent is selected from the group consisting of colloid stabilizers, particle interaction strengthening agents, and combinations thereof.

Statement 33. A zirconia green body of Statement 32, where the particle interaction strengthening agent is selected from the group consisting of polyethylene glycol (PEG), polyethylene oxide (PEO), polyvinylalcohol (PVA), methyl cellulose, polyacrylic acid, dextrin, poly-ethylene-co-propylene-glycol, and combinations thereof.

Statement 34. A zirconia green body according to any one of Statements 32 and/or 33, where the colloid stabilizers are selected from dispersants, protective colloids, and combinations thereof.

Statement 35. A zirconia green body of Statement 32, where the colloid stabilizer is selected from the group consisting of organocarboxylic acids (e.g., polyoxocarboxylic acids such as, for example, $CH_3$-[O—($CH_2CH_2$)]$_x CO_2H$ and salts thereof, where x is 1 to 120, 1 to 50, or 1 to 30), amino acids, organoamines, organoalcohols and organosilanes.

Statement 36. A zirconia green body of Statement 35, where the dispersant selected from the group consisting of 2-[2-(2-methoxyethoxy)ethoxy]acetic acid (TODA), 2-(2-methoxyethoxy)acetic acid (DOHA), O-(2-carboxyethyl)-O'-methyl-undecaethylene glycol, methoxypolyethylene glycol propionic acid (e.g., having a molecular weight of 5,000), 3,6,9-trioxaundecanedioic acid, polyacrylic acid, bicine, dodecyl amine, tetradecyl methyl amine, cetyl trimethyl ammonium bromide (CTAB), ammonium polyacrylate, polyethylene glycol dodecyl ether, trimethoxy(propyl) silane, 2-[(acetoxy(polyethyleneoxy)propyl]triethoxysilane and 2-[methoxy(triethyleneoxy)propyl]trimethoxysilane, and combinations thereof.

Statement 37. A zirconia green body according to any one or more of Statements 31 to 36, where the processing agent is 2% by weight TODA and/or ESD and 0.1% by weight PEG35K and 0.05% by weight PVA or 0.5% percent by weight PEG35k and 0.05% by weight PVA, where the percent by weight values are based on the total weight of the nanoparticles in the zirconia green body.

Statement 38. A zirconia green body according to any one or more of Statements 31 to 37, where the amount of the processing agent is 1.5 to 3.3% by weight based on the total weight of the nanoparticles in the zirconia green body.

Statement 39. A zirconia green body according to any one or more of Statements 22 to 38, where the zirconia green body is translucent and has a transmittance at 560 nm wavelength of 50 to 70% for a 1 to 2 mm thick sample of the zirconia green body.

Statement 40. A zirconia green body according to any one or more of Statements 22 to 39, where the zirconia green body has an opalescence of 20 to 30 for a 1 to 2 mm thick sample of the zirconia green body.

Statement 41. A zirconia green body of one or more of Statements 22 to 40, where the zirconia green body exhibits a Vickers hardness of 35 to 70 kg/mm$^2$.

Statement 42. A zirconia green body according to any one or more of Statements 22 to 41, where the zirconia green body has a dimension of 10 to 30 mm in a direction perpendicular to the longest dimension of the zirconia green body (thickness).

Statement 43. A zirconia green body according to any one or more of Statements 22 to 42, where the zirconia green body has a longest dimension of 15 to 100 mm.

Statement 44. A pre-sintered ceramic body comprising a plurality of zirconia nanoparticles, where the pre-sintered ceramic body is porous, the pre-sintered ceramic body is translucent and has a transmittance at 560 nm wavelength of 40 to 60% for a 1 to 2 mm thick sample of the pre-sintered ceramic body, and the pre-sintered ceramic body has an opalescence of 25 to 35 for a 1 to 2 mm thick sample of the pre-sintered ceramic body.

Statement 45. A pre-sintered ceramic body of Statement 44, where the pre-sintered ceramic body has a density of 50 to 70% of the zirconium dioxide theoretical density.

Statement 46. A pre-sintered ceramic body of one of Statements 44 and/or 45, where in the zirconia nanoparticles are in a tetragonal phase.

Statement 47. A pre-sintered ceramic body according to any one of Statements 44 and/or 45, where 10% or less of the zirconia nanoparticles are in cubic and/or monoclinic phase.

Statement 48. A pre-sintered ceramic body according to any one or more of Statements 44 to 47, where the pre-sintered ceramic body has a dimension of 10 to 30 mm in a direction perpendicular to the longest dimension of the pre-sintered ceramic body (thickness).

Statement 49. A pre-sintered ceramic body according to any one or more of Statements 44 to 48, where the pre-sintered ceramic body has a longest dimension of 15 to 100 mm.

Statement 50. A zirconia dental ceramic, where at least 95% of all grains by volume have a size of 10 nm to 300 nm and the average grain size is 40 nm to 150 nm, the density of the zirconia dental ceramic has a density that is at least 99.5% of zirconium dioxide theoretical density, and the zirconia dental ceramic is opalescent.

Statement 51. A zirconia dental ceramic of Statement 50, where the zirconia dental ceramic is translucent and has a transmittance at 560 nm wavelength of 25 to 50% for a 1 to 2 mm thick sample of the zirconia dental ceramic.

Statement 52. A zirconia dental ceramic according to any one of Statements 50 and/or 51, where the zirconia dental ceramic has an opalescence of 9 or greater for a 1 to 2 mm thick sample of the zirconia dental ceramic.

Statement 53. A zirconia dental ceramic according to any one or more of Statements 50 to 52, where the zirconia dental ceramic has an average flexural strength of 1200 MPa or greater.

Statement 54. A zirconia dental ceramic according to any one or more of Statements 50 to 53, where the zirconia dental ceramic has an average tensile strength of 500 MPa or greater.

Statement 55. A dental article formed from a zirconia dental ceramic of the present disclosure (e.g., the zirconia dental ceramic of Statement 50) or a formable gel of the present disclosure (e.g., a formable gel of Statement 1).

Statement 56. A dental article of Statement 55, where the dental article is a blank or smart blank.

Statement 57. A dental article of Statement 55, where the dental article is a dental restoration.

Statement 58. A dental article of Statement 57, where the dental restoration is selected from full-contour FPDs (fixed partial dentures), bridges, implant bridges, multi-unit frameworks, abutments, crowns, partial crowns, veneers, inlays, onlays, orthodontic retainers, space maintainers, tooth replacement appliances, splints, dentures, posts, teeth, jackets, facings, facets, implants, cylinders, and connectors.

Statement 59. A method of making a gel of the present disclosure (e.g., a gel of Statement 1) comprising: a) providing an aqueous suspension comprising zirconia nanoparticles having an average size of 10 to 30 nm and 95% or more of the zirconia nanoparticles by volume have a size of 45 nm or less, where the zirconia nanoparticles are present at less than 70% by weight of the aqueous suspension; and b) concentrating the aqueous suspension by removing water from the aqueous suspension with a semipermeable membrane, where the water removal is driven by intrinsically induced pressure or externally imposed pressure, until the suspension has zirconia nanoparticles present at 70 to 85% by weight of the aqueous suspension, whereby the gel is formed.

Statement 60. A method of Statement 59, where the aqueous suspension further comprises a processing agent.

Statement 61. A method according to Statement 60, where the total amount of the processing agents is present at 1.5% to 3.3% by weight based on the total weight of the nanoparticles in the aqueous suspension.

Statement 62. A method according to any one of Statements 59 to 61, where at least a portion of the processing agent is attached via at least one covalent bond to at least a portion of the zirconia nanoparticles.

Statement 63. A method of Statement 59, further comprising: attrition milling a starting aqueous suspension comprising zirconia nanoparticles having an average size greater than 50 nm, where the zirconia nanoparticles are present at 50% or greater by weight of the starting aqueous suspension based on the total weight of the starting aqueous suspension, and, optionally, subjecting the attrition milled starting aqueous suspension to centrifugation, to provide the aqueous suspension of a).

Statement 64. A method of Statement 63, where the starting aqueous suspension prior to attrition milling further comprises a colloidal stabilizer.

Statement 65. A method of Statement 64, where the total amount of the colloidal stabilizer is present at 0.5 to 2.5% by weight based on the total weight of zirconia nanoparticles in the starting aqueous suspension.

Statement 66. A method according to any one or more of Statements 63 to 65, where a particle interaction strengthening agent is added to the starting aqueous suspension after attrition milling.

Statement 67. A method according to Statement 66, where the total amount of the particle interaction strengthening agent is present at 0.1 to 1.5% by weight based on the total weight of the nanoparticles in the milled starting aqueous suspension.

Statement 68. A method according to Statement 59, where a starting aqueous suspension comprises zirconia nanoparticles having an average size greater than 50 nm, where the zirconia nanoparticles are present at less than 50% by weight of the starting aqueous suspension based on the total weight of the starting aqueous suspension and the method further comprises: i) concentrating the starting aqueous suspension by heating and/or applying sub-ambient pressure to the starting aqueous solution until the zirconia nanoparticles are present at 50% or greater by weight based on the total weight of the starting aqueous suspension; and ii) attrition milling the concentrated starting aqueous suspension from i) and, optionally, subjecting the attrition milled starting aqueous suspension to centrifugation, to provide the aqueous suspension of a).

Statement 69. A method according to Statement 68, where a colloidal stabilizer is added to the starting aqueous suspension prior to the concentration of the starting aqueous suspension.

Statement 70. A method according to Statement 69, where the total amount of the colloidal stabilizer is present at 0.5 to 2.5% by weight based on the total weight of the nanoparticles in the starting aqueous suspension.

Statement 71. A method according to any one or more Statements 68 to 70, where a particle interaction strengthening agent is added to the starting aqueous suspension after attrition milling.

Statement 72. A method according to Statement 71, where the total amount of the particle interaction strengthening agent is present at 0.1 to 1.5% by weight based on the total weight of the nanoparticles in the milled starting aqueous suspension.

Statement 73. A method according to any one or more of Statements 59 to 72, where the concentrating is carried out by an osmotic process.

Statement 74. A method according to Statement 73, where the osmotic solution used in the osmotic process is an aqueous polymer solution.

Statement 75. A method according to Statement 74, where the polymer of the aqueous polymer solution is selected from the group consisting of polyethylene glycol (PEG), poly-ethylene-co-propylene glycol, polyethylene imine (PEI), and combinations thereof.

Statement 76. A method according to any one or more of Statements 73 to 75, where the osmotic process is carried out with physical agitation of the aqueous suspension.

Statement 77. A method according to Statement 73, where the osmotic process comprises: a) placing the aqueous suspension comprising zirconia nanoparticles in an enclosure at least a portion of an external surface of which is a semipermeable membrane; b) contacting the enclosure with an osmotic solution such that the osmotic solution and the aqueous suspension are in fluid contact; c) agitating the aqueous suspension; and d) optionally, heating the osmotic solution.

Statement 78. A method according to Statement 59, where the concentrating is carried out by a tangential flow filtration process.

Statement 79. A method according to Statement 78, where the tangential flow filtration process comprises: a) flowing the aqueous suspension comprising zirconia nanoparticles through a channel at least a portion an external surface of which is the semipermeable membrane; b) repeating a) until the a desired amount of water is removed from the aqueous suspension comprising zirconia nanoparticles; and c) optionally, heating the aqueous suspension comprising zirconia nanoparticles.

Statement 80. A method according to Statement 78, where the semipermeable membrane is contacted with an osmotic solution.

Statement 81. A method of forming a green body according to the present disclosure (e.g., a green body according to Statement 22) comprising: a) providing a gel of the present disclosure (e.g., a gel of Statement 1); b) shaping the gel into a desired shape; and c) removing water from the shaped gel, whereby the zirconia green body having 2% to 5% water based on the weight of the zirconia green body is formed.

Statement 82. A method according to Statement 81, where the shaping comprises shaping the gel into an isotropically enlarged, uniform shape.

Statement 83. A method according to any one of Statements 81 and/or 82, where the removing is carried out by holding the shaped gel in a controlled-humidity and controlled-temperature environment.

Statement 84. A method according to Statement 83, where the humidity is 10 to 90% and the temperature is 20 to 50° C.

Statement 85. A method according to any one of Statements 81 and/or 82, where the removing is carried out by holding the shaped gel in two or more different controlled-humidity environments, where the humidity in each of the individual environments is 10 to 90% and different than the other individual environments and is decreased relative to the previous environment in which the gel was held.

Statement 86. A method according to Statement 85, where a first environment has a humidity of 70 to 90% and a second environment has a humidity of 10 to 30%.

Statement 87. A method according to Statement 86, where the removing is carried out by: i) holding the shaped gel in the first environment for 1 to 10 days; and ii) subsequently holding the shaped gel from i) in two or more other environments for 1 to 10 days, where the humidity in each of the other environments is from 30 to 90% and is decreased relative to the previous environment in which the gel was held and the last environment has a humidity of 10 to 30%.

Statement 88. A method of making a pre-sintered ceramic body of the present disclosure (e.g., a pre-sintered ceramic body according to Statement 44), comprising heating a zirconia green body of the present disclosure (e.g., a zirconia green body according to Statement 22) to a temperature of 400 to 1000° C.

Statement 89. A method according to Statement 88, where the zirconia green body is heated at a rate of 0.1 to 10° C./min.

Statement 90. A method of making a dental article of the present disclosure (e.g., a dental article according to Statement 55) comprising shaping a green body of the present disclosure (e.g., a green body according to Statement 22) or a pre-sintered ceramic body of the present disclosure (e.g., a pre-sintered ceramic body according to Statement 44) and heating the shaped green body or shaped pre-sintered ceramic body to a temperature according to 1000 to 1200° C., whereby the dental restoration is formed.

Statement 91. A method according to Statement 90, where the shaping of a zirconia green body of the present disclosure (e.g., a zirconia green body according to Statement 22) or a pre-sintered ceramic body of the present disclosure (e.g. a pre-sintered ceramic body according to Statement 44) is carried out using CAD/CAM, LPIM, or dental heat pressing.

The following examples are presented to illustrate the present disclosure. They are not intended to limiting in any matter.

Comparative Example 1

This example provides a description of comparison of drop casting prior art zirconia suspensions and nanozirconia suspensions of the present disclosure.

2 kg of 22 wt % (4.4 vol %) aqueous suspensions of yttria (3 mol %) stabilized zirconia nanoparticulate, containing 0 to 0.3% alumina (e.g., 0.25% alumina) by weight to solid zirconia, were stabilized by adding 2% TODA (obtained from Euticals GmbH) dispersants (2TODA) by weight to solid zirconia and surface modified at elevated temperature of 60° C. for 1 hour with constant stirring. The pH of such stabilized suspension was 2.5. The suspension was then concentrated from 22 wt % to 55 wt % (16.7 vol %) of solid loading with an Ika RV10 vacuum evaporator at 40° C. and 40 mbar for about 4 hours. The concentrated suspension was then attrition milled with 50 μm diameter yttria-stabilized zirconia beads at 3000 rpm rotation speed for 105 minutes, using Netzsch MiniCer attrition milling machine. Dynamic Light Scattering (DLS) measurement (Nano-ZS by Malvern) was used to monitor the deagglomeration of particles during the attrition milling process, as shown in FIG. 6A.

Cylindrical PTFE molds of 18 mm to 32 mm in diameter and 10 mm in height were prepared as it was previously established that it is impossible to produce viable drop cast samples much thicker than 7-8 mm even in green state from suspensions processed as above. From 5 to 15 g of slurry was poured into each mold depending on the desired final thickness. Then molds with suspension were put into an environmental chamber for curing and drying. For the first 72~120 hours, the humidity was above 85% and temperature was about 25° C. The drying time was determined by the thickness of the samples. The thicker samples took a longer time to dry without generating cracks. Then environmental humidity was decreased gradually to about 20% in 168 hours. The as-formed green bodies were ~49% of theoretical density. Light transmittance was 58% for 2 mm thick green body at 560 nm. Dried green bodies were subjected to organic burn out cycle in a burn-out furnace (Vulcan 3-550) by heating at a rate of 0.1° C./min to 240° C. and then 0.5° C./min to 550° C. or 700° C. and holding for 2 hours at that temperature. The obtained "brown" bodies (also having high light transmittance of about 50% at 560 nm for 1.8-2.0 mm thick samples) were then sintered in a dental furnace or Nabertherm HTC 08/16 furnace at a ramp rate of 10° C./min to 1100° C., hold for 2 hours and then furnace cooled to idle temperature or to room temperature, respectively. After sintering, the disk samples were from 12 to 23 mm in diameter and 1.5 mm in thickness.

The samples were then ground and polished down to thickness of 1.0 mm, to prepare samples for optical (transmittance and opalescence) measurements and 1.0-1.2 mm for biaxial flexural strength measurements. The measurement results are presented in Table 2 and compared with those of other examples. The number of sample size is 3 for optical measurements and at least 10 for biaxial flexural strength measurements.

TABLE 2

Physical properties of gel-formed articles.

|  | Comparative Example 1: Drop cast, no processing agent | Comparative Example 2: Drop cast, with 1.0% PEG35k | Example 2A: Osmotic gel, with 1.0% PEG35k | Example 5A: Osmotic gel, with 0.1% PEG35K + 0.05% PVA |
|---|---|---|---|---|
| Sintering condition | 1100° C./2 h 10° C./min | 1100° C./2 h 10° C./min | 1100° C./2 h 3° C./min | 1100° C./2 h 3° C./min |
| Relative density, % | 99.78 ± 0.03 | 99.70 | 99.82 ± 0.07 | 99.87 ± 0.06 |
| In-line Transmission at 560 nm, % | 4.1 ± 0.6 | 9.0 | 2.5 ± 0.8 | 2.5 ± 0.1 |
| All forwarding T at 560 nm, % | 39.7 ± 0.4 | 40.6 | 38.3 ± 1.2 | 37.9 ± 0.2 |
| Opalescence | 17.4 ± 0.2 | 18.2 | 14.6 ± 0.9 | 15.2 ± 0.2 |
| Grain size, nm | 90 ± 10 | 85 ± 11 | 92 ± 15 | N/A |
| Biaxial strength, MPa (# of samples, min, max) | 1900 ± 156 (10, 1599, 2047) | N/A | N/A | 1807 ± 182 (11, 1585, 2123) |

Comparative Example 2

This example provides a description of comparison of drop casting prior art zirconia suspensions and nanozirconia suspensions of the present disclosure.

The suspension preparation, concentration and attrition-milling steps were identical to Comparative Example 1. After attrition milling and before mold casting, 1.0% by weight to solid zirconia of polyethylene glycol with number average molecular weight of 35,000 (PEG35K, obtained from SigmaAldrich) was admixed to the suspension and homogenized on shaking table. Identical mold casting, drying, organic burn out, sintering, grinding and polishing steps were then conducted as described in Comparative Example 1. The transmittance and opalescence measurements were then performed and the results are shown and compared in Table 2.

Comparative Example 3

This example provides a description of good starting suspensions and bad starting suspensions before and after attrition milling.

FIGS. 11A, 11B, 12A, and 12B show comparison of two suspensions of a similar solid loading of about 55 wt % and 0.5 wt %: a typical nanosuspension meeting the requirements of this disclosure ("good" suspension in FIGS. 11A, 11B, 12A and 12B) and unacceptably agglomerated batch of nanosuspension not processable by methods described herein ("bad" suspension in FIGS. 11A, 11B, 12A, and 12B). After TODA surface modification and concentration to 55 wt %, both suspensions were attrition milled for up to 2 hours. As it can be clearly seen, the good suspension gradually turned to be translucent from milky appearance during attrition milling, while the bad suspension remained milky. It is important to note that after 105 min of attrition milling the average particle size in a good suspension was 20 nm and in a bad suspension was 40 nm.

Example 1

This example provides a description of making and characterizing nanozirconia gels and zirconia green bodies of the present disclosure.

The suspension preparation, concentration and attrition-milling steps were identical to Comparative Example 1. The said 55 wt % 2TODA zirconia suspension were then further concentrated to form a gel using osmotic processing method as described below: 50-200 grams of 55 wt % (16.7 vol %) suspension was poured in a dialysis membrane tubing (Spectra/Par dialysis membrane MWCO 6000-8000, tubing flat width 50 mm), while leaving ⅓ to ¼ of the tubing unfilled. The two ends of the tubing were closed by two clip closures. The loaded tubing was then immersed in a 20 wt % polyethylene glycol (molecular weight 35,000) (PEG35K)/water solution in a closed container. The container was then placed on a shaking table and continuously shaken at 125 rpm for 24 hours. The obtained gel is translucent and soft, with 81 wt % (41.1 vol %) solid loading. The tactile feel of the gel is consistent with vacuum grease. The assessment of the gel softness and gel formability is presented in Table 3, with comparison to other examples.

Figure 10A:
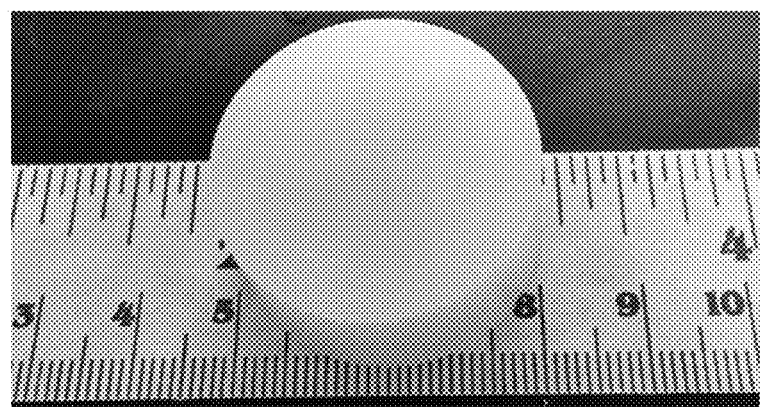
FIGS. 10A, 10B, and 10C. The cylindrical green body formed in Example 1 A); stained and the glazed molar crown of Example 21C B); stained and the glazed molar crown of Example 21C, picture taken from a different angle C).

Cylindrical PTFE molds of 27 to 37 mm in diameter and 30 to 40 mm in height were prepared. Demolding agent was applied on the surfaces of each molds and then carefully wiped off, so that a thin layer of the demolding agent was left on the surfaces. The said gel was further homogenized with a Thinky Planetary Mixer at 1000 rpm for 60 seconds. 30 to 60 gram zirconia gel was then fed into each mold with a Teflon coated spatula. The loaded molds were put in a centrifuging machine (Legend XT by Thermo Scientific) and centrifugal cast at 4300 rpm for 5 minutes. The mold was then taken out and placed in an environmental chamber for drying at 25° C. For the first 168 hours, the chamber humidity was set to be no lower than 80% and then gradually dropped to 20% in the next 168 hours. The obtained dried zirconia green bodies were cylinders with 24 to 32 mm in diameter and 14 to 18 mm in height, as shown in FIG. 10A. Green bodies that survived the said drying process had no visible cracks and bubbles. Survival rate of the green bodies 32 mm in diameter and 14 to 18 mm in thickness is summarized in Table 3 in comparison with other examples. It should be noted while thickness of the samples made by drop-casting was below 2 mm, thickness of the samples formed from gel was exceeding 14 mm and approaching 20 mm.

TABLE 3

Examples of gels with PEG/PVA additives.

| Suspension | Processing agent | Osmotic time, hr | Gel loading*, wt % (vol %) | Gel softness/ rigidity | Gel formability ranking | PEG35K vs PEG20K | Green body drying survival rate, % |
|---|---|---|---|---|---|---|---|
| 2TODA | EX1: No processing agent | 24 | ~81 (41.1) | soft | 4 | | <70 |
| | EX2: 1.0% PEG | 24 | ~76 (34.2) | very soft | 5 | EX2A: 35k | 70-80 |
| | | | | | | EX2B: 20k | >80 |
| | EX3: 1.0% PEG + 0.05% PVA | 22 | ~77 (35.4) | soft | 4 | EX3A: 35k | >80 |
| | | | | | | EX3B: 20k | >80 |
| | EX4: 0.5% PEG+ 0.05% PVA | 20 | ~78 (36.8) | soft | 4 | EX4A: 35k | <70 |
| | | | | | | EX4B: 20k | >80 |
| | EX5: 0.1% PEG + 0.05% PVA | 18 | ~78 (36.8) | semi-soft | 2-3 | EX5A: 35k | >80 |
| | | | | | | EX5B: 20k | <70 |
| | EX6: 0.05% PVA | 17 | ~78 (36.8) | semi-rigid to rigid | 0 | | N.A. (too rigid) |
| 2ESD | EX7: No processing agent | 22 | ~77 (35.4) | semi-soft | 2-3 | | 0 |
| | EX8: 1.0% PEG | 22 | ~75 (33.0) | soft to semi-soft | 3 | EX8A: 35k | >80 |
| | | | | | | EX8B: 20k | >80 |
| | EX9: 1.0% PEG + 0.05% PVA | 19 | ~75 (33.0) | soft to semi-soft | 3 | EX9A: 35k | >80 |
| | | | | | | EX9B: 20k | <70 |
| | EX10: 0.5% PEG + 0.05% PVA | 19 | ~76 (34.2) | semi-soft | 2-3 | EX10A: 35k | <70 |
| | | | | | | EX10B: 20k | <70 |
| | EX11: 0.1% PEG + 0.05% PVA | 18 | ~76 (34.2) | soft to semi-soft | 3 | EX11A: 35k | >80 |
| | | | | | | EX11B: 20k | <70 |
| | EX12: 0.05% PVA | 17 | ~78 (36.8) | Rigid | 0 | | N.A. (too rigid) |

*Not the highest loading achievable. Higher gel loading can be achieved with extended osmotic time.

Example 2

This example provides a description of making and characterizing nanozirconia gels and zirconia green bodies of the present disclosure.

The 2TODA zirconia suspension preparation, concentration, attrition-milling steps and gel preparation steps were identical to Example 1 with the same amount of osmotic time of 24 hours. However, after attrition milling and before placing the suspension to dialysis tubing for osmosis, 1.0% by weight to solid zirconia of polyethylene glycol with number average molecular weight of 35,000 (PEG35K) (Example 2A) or 20,000 (PEG20K, obtained from SigmaAldrich) (Example 2B) was admixed to the suspension and homogenized on shaking table. The mixture was then loaded in dialysis tubing and osmosized for 24 hours. The obtained gel is translucent and very soft, with 76 wt % (34.2 vol %) solid loading. The gel was then centrifugal cast and dried identically as described in Example 1. The gel solid loading, gel softness, gel formability and green body survival rate are presented in Table 3.

The 24 mm diameter cylindrical green bodies obtained from example 2A were ground to 3.5 mm thick and then subjected to organic burn out cycle in a burn-out furnace (Vulcan 3-550) by heating at a rate of 0.1° C./min to 240° C. and then 0.5° C./min to 700° C. and holding for 2 hours at that temperature. The obtained "brown" bodies were then sintered in a dental furnace or Nabertherm HTC 08/16 furnace at a ramp rate of 3° C./min to 1100° C., hold for 2 hours and then furnace cooled to idle temperature or to room temperature. After sintering, the samples are ~18 mm in diameter and ~2.8 mm in thickness. The sintered samples were further ground and polished down to thickness of 1.0 mm to prepare samples for optical (transmittance and opalescence) measurements. The measurement results are presented in Table 2 and compared with those of other examples. The number of sample size is 3 for optical measurements.

Example 3

This example provides a description of making and characterizing nanozirconia gels and zirconia green bodies of the present disclosure.

The 2TODA zirconia suspension preparation, concentration and attrition-milling steps and gel preparation steps were identical to Example 1 with osmotic time of 22 hours. However, after attrition milling and before placing the suspension to dialysis tubing, 1.0% by weight to solid zirconia of PEG35K (Example 3A) or PEG20K (Example 3B) was admixed to the suspension, followed by admixing 0.05% by weight to solid zirconia of polyvinylalcohol with weight average molecular weight 9,000 to 10,000 (PVA, obtained from SigmaAldrich). After being shaken and homogenized, the mixture was then loaded in dialysis tubing and osmosized for 22 hours. The obtained gel was translucent and soft, with 77 wt % (35.4 vol %) solid loading. The gel was then centrifugal cast and dried identically as described in Example 1. The gel solid loading, gel softness, gel formability and green body survival rate are presented in Table 3.

Example 4

This example provides a description of making and characterizing nanozirconia gels and zirconia green bodies of the present disclosure.

The 2TODA zirconia suspension preparation, concentration and attrition-milling steps and gel preparation steps were identical to Example 1 with osmotic time of 20 hours. However, after attrition milling and before placing the suspension to dialysis tubing, 0.5% by weight to solid zirconia of PEG35K (Example 4A) or PEG20K (Example 4B) was admixed to the suspension, followed by admixing 0.05% by weight to solid zirconia of PVA. After being shaken and homogenized, the mixture was then loaded in dialysis tubing and osmosized for 20 hours. The obtained gel was translucent and soft, with 78 wt % (36.8 vol %) solid loading. The gel was then centrifugal cast and dried identically as described in Example 1. The gel solid loading, gel softness, gel formability and green body survival rate are presented in Table 3.

Example 5

This example provides a description of making and characterizing nanozirconia gels and zirconia green bodies of the present disclosure.

The 2TODA zirconia suspension preparation, concentration and attrition-milling steps and gel preparation steps were identical to Example 1 with osmotic time of 18 hours. However, after attrition milling and before placing the suspension to dialysis tubing, 0.1% by weight to solid zirconia of PEG35K (Example 5A) or PEG20K (Example 5B) was admixed to the suspension, followed by admixing 0.05% by weight to solid zirconia of PVA. After being shaken and homogenized, the mixture was then loaded in dialysis tubing and osmosized for 18 hours. The obtained gel was translucent and semi-soft, with 78 wt % (36.8 vol %) solid loading. The gel was then centrifugal cast and dried identically as described in Example 1. The gel solid loading, gel softness, gel formability and green body survival rate are presented in Table 3.

To measure the optical properties and biaxial flexural strength, two sizes of cylindrical green bodies of example 5A were prepared: 24 mm diameter green bodies for optical measurements using 27 mm diameter PTFE molds and 18 mm diameter green bodies for biaxial flexural strength measurement using 22 mm diameter PTFE molds. Both cylindrical green bodies were ground to 2.5 mm thick and then subjected to organic burn out cycle in a burn-out furnace (Vulcan 3-550) by heating at a rate of 0.1° C./min to 240° C. and then 0.5° C./min to 700° C. and holding for 2 hours at that temperature. The obtained "brown" bodies were then sintered in a dental furnace or Nabertherm HTC 08/16 furnace at a ramp rate of 3° C./min to 1100° C., hold for 2 hours and then furnace cooled to idle temperature or to room temperature, respectively. After sintering, the samples were ~18 mm and ~13 mm in diameter, respectively, and ~2.0 mm in thickness. The sintered samples were further ground and polished down to thickness of 1.0 mm to prepare samples for optical (transmittance and opalescence) measurements and 1.0-1.2 mm for biaxial flexural strength measurements. The measurement results are presented in Table 2 and compared with those of other examples. The number of sample size is 3 for optical measurements and at least 10 for biaxial flexural strength measurements.

Example 6

This example provides a description of making and characterizing nanozirconia gels and zirconia green bodies of the present disclosure.

The 2TODA zirconia suspension preparation, concentration and attrition-milling steps and gel preparation steps were identical to Example 1 with osmotic time of 17 hours. However, after attrition milling and before placing the suspension to dialysis tubing, 0.05% by weight to solid zirconia of PVA was admixed to the suspension. After being shaken and homogenized, the mixture was then loaded in dialysis tubing and osmosized for 17 hours. The obtained gel was translucent but rigid, with 78 wt % (36.8 vol %) solid loading. This rigid gel became non-formable, as described in Table 3.

Example 7

This example provides a description of making and characterizing nanozirconia gels and zirconia green bodies of the present disclosure.

2 kg of 55 wt % (16.7 vol %) aqueous suspensions of yttria (3 mol %) stabilized zirconia nanoparticulate, containing 0 to 0.3% alumina (e.g., 0.25% alumina) by weight to solid zirconia by weight to solid zirconia and 2% of an ESD (2ESD suspension) by weight to solid zirconia. The pH of such a stabilized suspension was 5.1. The suspension was then attrition milled with 50 μm diameter yttria-stabilized zirconia beads at 3000 rpm rotation speed for 105 minutes, using Netzsch MiniCer attrition milling machine. Dynamic Light Scattering (DLS) measurement (Nano-ZS by Malvern) was used to monitor the deagglomeration of particles during the attrition milling process, as shown in FIG. 6B.

The attrition milled 55 wt % 2ESD zirconia suspension were then further concentrated to 75-80 wt % (33-40 vol %) zirconia content using the osmotic processing as described in Example 1. In this example, 22 hour osmotic time was applied and the obtained gel was translucent and semi-soft, with 77 wt % (35.4 vol %) solid loading. The gel was then centrifugal cast and dried identically as described in Example 1. The gel solid loading, gel softness, gel formability and green body survival rate are presented in Table 3.

Example 8

This example provides a description of making and characterizing nanozirconia gels and zirconia green bodies of the present disclosure.

The 2ESD zirconia suspension attrition milling and gel preparation steps were identical to Example 7 with the same amount of osmotic time of 22 hours. However, after attrition milling and before placing the suspension to dialysis tubing, 1.0% by weight to solid zirconia of PEG35K (Example 8A) or PEG20K (Example 8B) was admixed to the suspension and homogenized on shaking table. The mixture was then loaded in dialysis tubing and osmosized for 22 hours. The obtained gel was translucent and soft to semi-soft, with 75 wt % (33.0 vol %) solid loading. The gel was then centrifugal cast and dried identically as described in Example 1. The gel solid loading, gel softness, gel formability and green body survival rate are presented in Table 3.

Example 9

This example provides a description of making and characterizing nanozirconia gels and zirconia green bodies of the present disclosure.

The 2ESD zirconia suspension attrition milling and gel preparation steps were identical to Example 7 with osmotic time of 19 hours. However, after attrition milling and before placing the suspension to dialysis tubing, 1.0% by weight to solid zirconia of PEG35K (Example 9A) or PEG20K (Example 9B) was admixed to the suspension, followed by admixing 0.05% by weight to solid zirconia of PVA. After being shaken and homogenized, the mixture was then loaded in dialysis tubing and osmosized for 19 hours. The obtained gel was translucent and soft to semi-soft, with 75 wt % (33.0 vol %) solid loading. The gel was then centrifugal cast and dried identically as described in Example 1. The gel solid loading, gel softness, gel formability and green body survival rate are presented in Table 3.

Example 10

This example provides a description of making and characterizing nanozirconia gels and zirconia green bodies of the present disclosure.

The 2ESD zirconia suspension attrition milling and gel preparation steps were identical to Example 7 with osmotic time of 19 hours. However, after attrition milling and before placing the suspension to dialysis tubing, 0.5% by weight to solid zirconia of PEG35K (Example 10A) or PEG20K (Example 10B) was admixed to the suspension, followed by admixing 0.05% by weight to solid zirconia of PVA. After being shaken and homogenized, the mixture was then loaded in dialysis tubing and osmosized for 19 hours. The obtained gel was translucent and semi-soft, with 76 wt % (34.2 vol %) solid loading. The gel was then centrifugal cast and dried identically as described in Example 1. The gel solid loading, gel softness, gel formability and green body survival rate are presented in Table 3.

Example 11

This example provides a description of making and characterizing nanozirconia gels and zirconia green bodies of the present disclosure.

The 2ESD zirconia suspension attrition milling and gel preparation steps were identical to Example 7 with osmotic time of 18 hours. However, after attrition milling and before placing the suspension to dialysis tubing, 0.1% by weight to solid zirconia of PEG35K (Example 11A) or PEG20K (Example 11B) was admixed to the suspension, followed by admixing 0.05% by weight to solid zirconia of PVA. After being shaken and homogenized, the mixture was then loaded in dialysis tubing and osmosized for 19 hours. The obtained gel was translucent and soft to semi-soft, with 76 wt % (34.2 vol %) solid loading. The gel was then centrifugal cast and dried identically as described in Example 1. The gel solid loading, gel softness, gel formability and green body survival rate are presented in Table 3.

Example 12

This example provides a description of making and characterizing nanozirconia gels and zirconia green bodies of the present disclosure.

The 2ESD zirconia suspension attrition milling and gel preparation steps were identical to Example 7 with osmotic time of 17 hours. However, after attrition milling and before placing the suspension to dialysis tubing, 0.05% by weight to solid zirconia of PVA was admixed to the suspension. After being shaken and homogenized, the mixture was then loaded in dialysis tubing and osmosized for 17 hours. The obtained gel was translucent but rigid, with 78 wt % (36.8 vol %) solid loading. This rigid gel became non-formable, as described in Table 3.

Example 13

This example provides a description of making and characterizing nanozirconia gels and zirconia green bodies of the present disclosure.

The 2TODA zirconia suspension preparation, concentration and attrition-milling steps and gel preparation steps were identical to Example 1 with osmotic time of 32 hours. However, after attrition milling and before placing the suspension to dialysis tubing for osmosis, 1.0% by weight to solid zirconia of polyethylene oxide with average molecular weight of 100,000 (PEO100K, obtained from SigmaAldrich) was admixed to the suspension and homogenized on shaking table. The mixture was then loaded in dialysis tubing and osmosized for 32 hours. The obtained gel was translucent and soft, with 74 wt % (31.8 vol %) solid loading.

Cylindrical Silicone molds of 25 mm in diameter and 30 mm in height were prepared. The said gel was further homogenized with a Thinky Planetary Mixer at 1000 rpm for 60 seconds. About 30 gram gel was placed into each mold with a Teflon coated spatula until it was totally filled. The mold was then tightly capped with a silicone cup. The loaded molds were then sealed in plastic bags and placed in a Cold Isostatic Pressing (CIP) machine. The CIP pressure was set to 30 ksi for 5 minutes. The mold was then taken out and placed in an environmental chamber for drying as described in Example 1. The gel solid loading, gel softness, gel formability and green body survival rate are presented in Table 4.

TABLE 4

Examples of binders that didn't provide gels.

| Suspension | Binder | Osmotic time, hr | Gel loading, wt % (vol %) | Gel softness/ rigidity | Gel formability ranking | Green body drying survival rate, % |
|---|---|---|---|---|---|---|
| 2TODA | EX13: 1.0% PEO100K | 32 | ~74 (31.8) | Soft | 4-5 | 0 |
|  | EX14: 0.2% MC | 24 | ~80 (39.6) | Semi-soft to semi-rigid | 1 | 0 |
|  | EX15: 1.0% PEG35K + 0.2% MC | 24 | ~74 (31.8) | soft to semi-soft | 3 | 0 |
| 2ESD | EX16: 1.0% PEO100K | 32 | ~76 (34.2) | Soft | 4 | 0 |
|  | EX17: 0.2% MC | 22 | ~76 (34.2) | semi-soft | 2 | 0 |
|  | EX18: 1.0% PEG35K + 0.2% MC | 22 | ~73 (30.7) | soft to semi-soft | 3 | 0 |

Formation: CIP, 30 ksi, 5 mins

Example 14

This example provides a description of making and characterizing nanozirconia gels and zirconia green bodies of the present disclosure.

The 2TODA zirconia suspension preparation, concentration and attrition-milling steps and gel preparation steps were identical to Example 1 with osmotic time of 24 hours. However, after attrition milling and before placing the suspension to dialysis tubing for osmosis, 0.2% by weight to solid zirconia of methylcellulose (MC, obtained from Dow Chemicals) with number average molecular weight of 41,000 was admixed to the suspension and homogenized on shaking table. The mixture was then loaded in dialysis tubing and osmosized for 24 hours. The obtained gel was translucent and semi-soft to semi-rigid, with 80 wt % (39.6 vol %) solid loading. The gel was then CIP cast and dried identically as described in Example 13. The gel solid loading, gel softness, gel formability and green body survival rate are presented in Table 4.

Example 15

This example provides a description of making and characterizing nanozirconia gels and zirconia green bodies of the present disclosure.

The 2TODA zirconia suspension preparation, concentration and attrition-milling steps and gel preparation steps were identical to Example 1 with osmotic time of 24 hours. However, after attrition milling and before placing the suspension to dialysis tubing, 1.0% by weight to solid zirconia of PEG35K was admixed to the suspension, followed by admixing 0.2% by weight to solid zirconia of methylcellulose (MC). After being shaken and homogenized, the mixture was then loaded in dialysis tubing and osmosized for 24 hours. The obtained gel was translucent and soft to semi-soft, with 74 wt % (31.8 vol %) solid loading. The gel was then CIP cast and dried identically as described in Example 13. The gel solid loading, gel softness, gel formability and green body survival rate are presented in Table 4.

Example 16

This example provides a description of making and characterizing nanozirconia gels and zirconia green bodies of the present disclosure.

The 2ESD zirconia suspension attrition milling and gel preparation steps were identical to Example 7 with osmotic time of 32 hours. However, after attrition milling and before placing the suspension to dialysis tubing for osmosis, 1.0% by weight to solid zirconia of PEO100K was admixed to the suspension and homogenized on shaking table. The mixture was then loaded in dialysis tubing and osmosized for 32 hours. The obtained gel was translucent and soft, with 76 wt % (34.2 vol %) solid loading. The gel was then CIP cast and dried identically as described in Example 13. The gel solid loading, gel softness, gel formability and green body survival rate are presented in Table 4.

Example 17

This example provides a description of making and characterizing nanozirconia gels and zirconia green bodies of the present disclosure.

The 2ESD zirconia suspension attrition milling and gel preparation steps were identical to Example 7 with osmotic time of 22 hours. However, after attrition milling and before placing the suspension to dialysis tubing for osmosis, 0.2% by weight to solid zirconia of methylcellulose (MC) was admixed to the suspension and homogenized on shaking table. The mixture was then loaded in dialysis tubing and osmosized for 22 hours. The obtained gel was translucent and semi-soft, with 76 wt % (34.2 vol %) solid loading. The gel was then CIP cast and dried identically as described in Example 13. The gel solid loading, gel softness, gel formability and green body survival rate are presented in Table 4.

Example 18

This example provides a description of making and characterizing nanozirconia gels and zirconia green bodies of the present disclosure.

The 2ESD zirconia suspension attrition milling and gel preparation steps were identical to Example 7 with osmotic time of 22 hours. However, after attrition milling and before placing the suspension to dialysis tubing, 1.0% by weight to solid zirconia of PEG35K was admixed to the suspension, followed by admixing 0.2% by weight to solid zirconia of methylcellulose (MC). After being shaken and homogenized, the mixture was then loaded in dialysis tubing and osmosized for 22 hours. The obtained gel was translucent and soft to semi-soft, with 73 wt % (30.7 vol %) solid loading. The gel was then CIP cast and dried identically as described in Example 13. The gel solid loading, gel softness, gel formability and green body survival rate are presented in Table 4.

Example 19

This example provides a description of making and characterizing nanozirconia gels of the present disclosure.

Figure 10B:
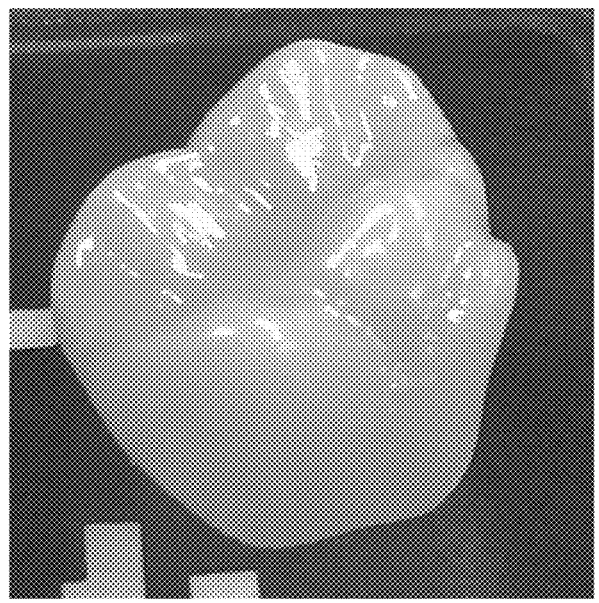
Figure 10C:
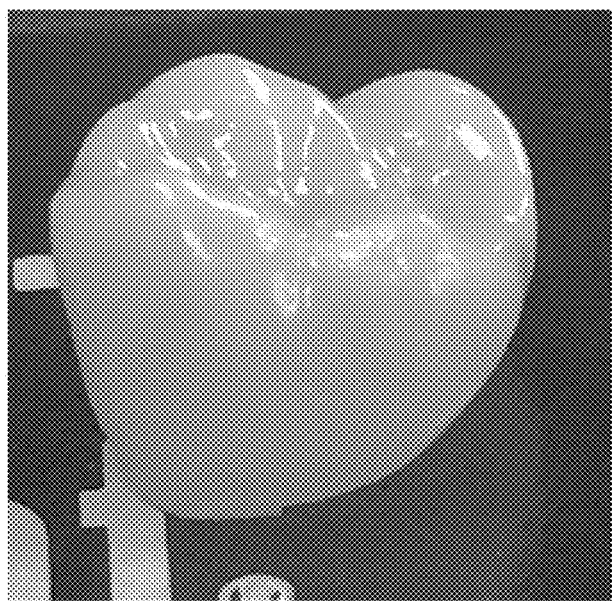
Figure 11A:
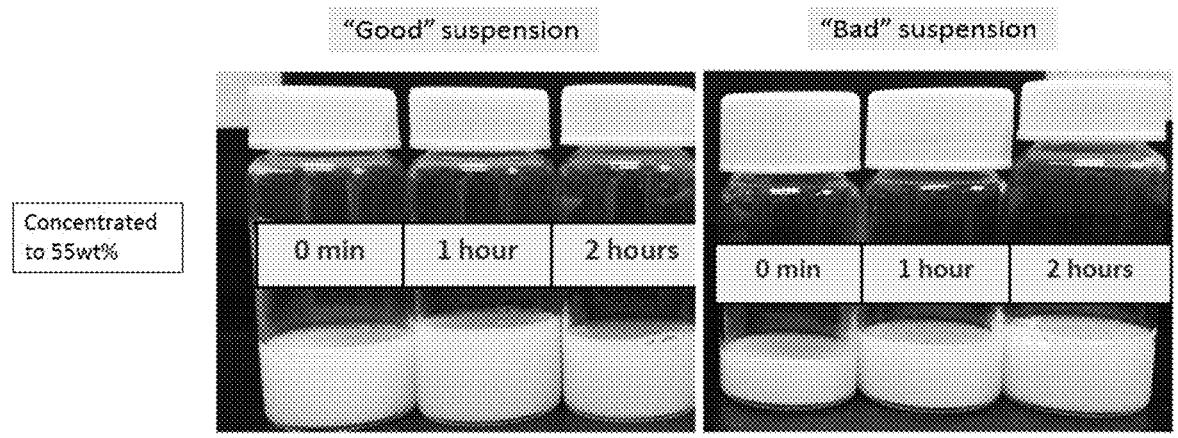
FIGS. 11A and 11B. Appearance of good (left) vs. bad (right) starting suspensions before (0 min) and after attrition milling for 1 hour and 2 hours, A) as-prepared 55 wt % suspension B) 0.5 wt % suspension diluted from 55 wt %.
Figure 11B:
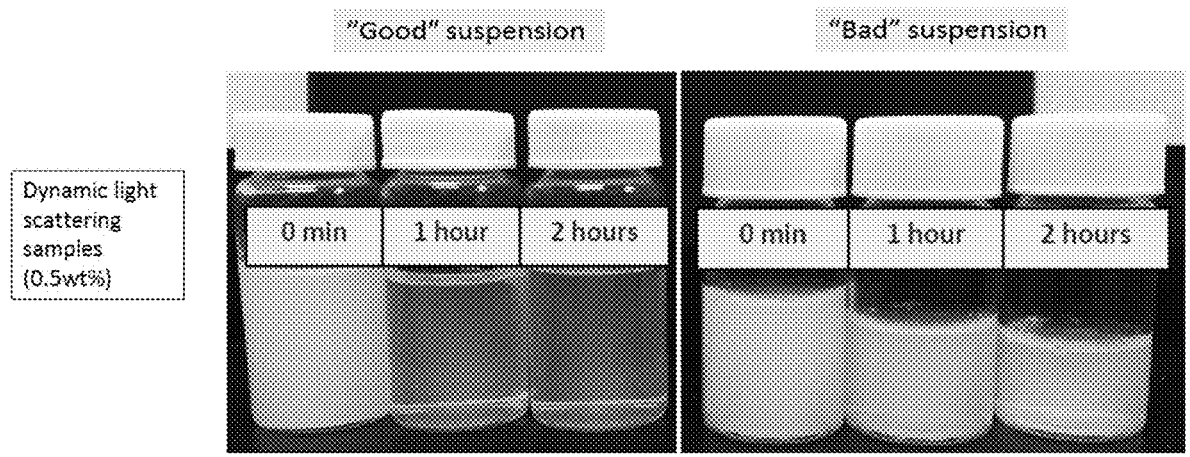
Figure 12A:
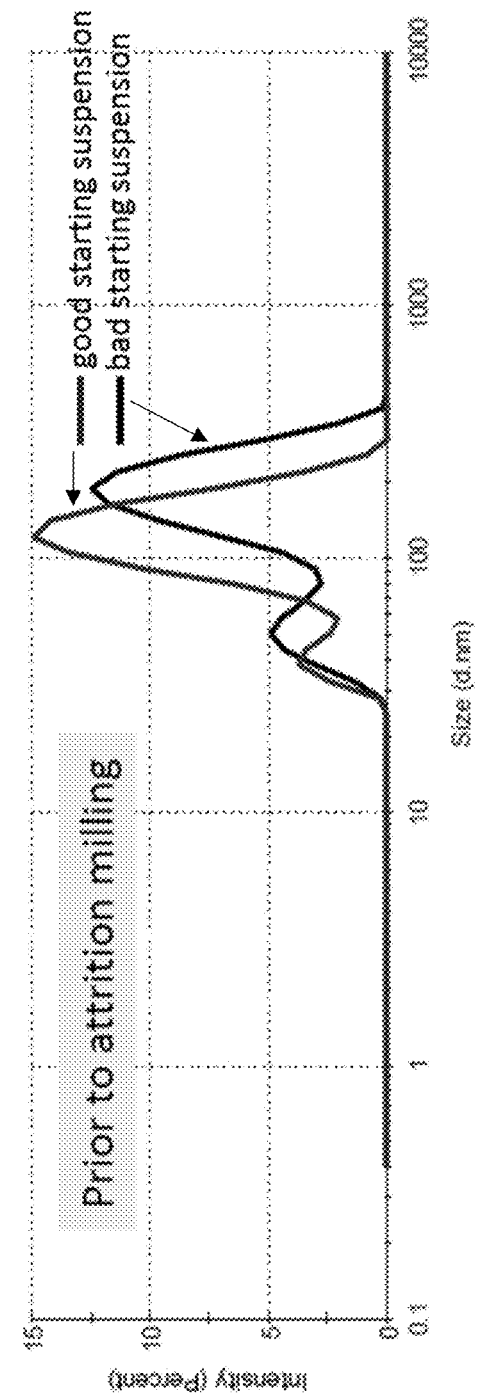
FIGS. 12A and 12B. Particle size distribution by intensity of good vs. bad starting suspensions, A) before and B) after attrition milling for 105 minutes.
Figure 12B:
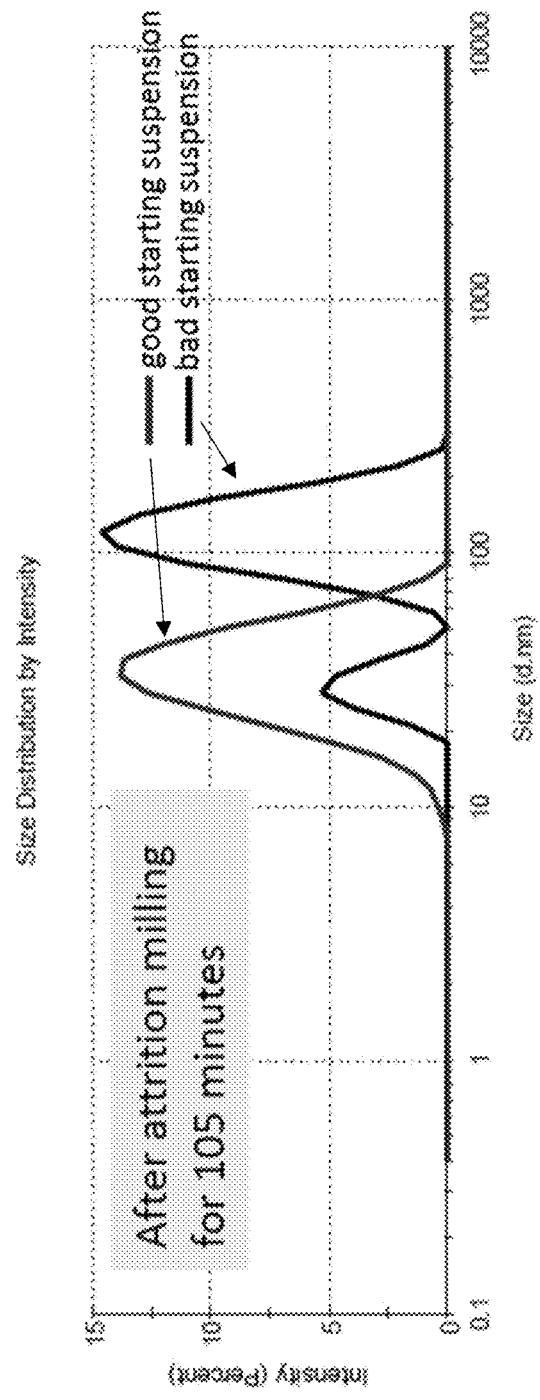

The 2ESD zirconia suspension attrition milling and gel preparation steps were identical to Example 7 with osmotic time of 16 hours and smaller MWCO dialysis membrane Gel prepared from Example 5A was centrifugal cast and dried as describe in Example 1. The obtained green bodies were cylinders with ~32 mm in diameter and 14-18 mm in height and free of cracks or bubbles by visual examination. One of the sides of these cylindrically shaped blanks was flattened and glued to Katana-compatible mandrel by superglue. Katana Dental CAD/CAM System (Model H18) was used to mill these green blanks into standard molar crowns using enlargement factors of 1.15-1.2. The obtained crack-free green crowns were then subjected to organics burn-out by heating at a rate of 0.1° C./min to 240° C., then 0.5° C./min to 700° C. and holding for 2 hours at that temperature resulting in a crack free "brown" crowns. The "brown" crowns were then sintered at a ramp rate of 3° C./min to 1100° C., hold for 2 hours. The as-sintered molar crowns (Example 21A) were then glazed (Example 21B) or stained and glazed to match Vita A1 shade guide as shown in FIG. 10B,C (Example 21C).

The sample information is summarized in Table 5.

TABLE 5

Dental restorations milled from gel-formed green bodies and finished using conventional equipment and procedures.

| Example | Dispersant | Processing agent | Sintering | Post treatment |
|---|---|---|---|---|
| EX21: crowns produced with gel formed by EX5A | 2TODA | 0.1% PEG35K + 0.05% PVA | 1100° C. for 2 hrs, 3° C./min | EX21A: As sintered EX21B: Glazed EX21C: Stained to Vita A1 shade and glazed |
| EX22: crowns produced with gel formed by EX3A | 2TODA | 1.0% PEG35K + 0.05% PVA | 1100° C. for 2 hrs, 3° C./min | EX22A: Glazed EX22B: Stained to Vita A3 shade and glazed | tubing (MWCO 1000). However, after attrition milling and before placing the suspension to dialysis tubing, 0.05% by weight to solid zirconia of polyacrylic acid with weight average molecular weight 1800 (PAA, obtained from SigmaAldrich) was admixed to the suspension. After being shaken and homogenized, the mixture was then loaded in dialysis tubing and osmosized for 16 hours. The obtained gel was translucent and semi-soft, with 77 wt % (35.4 vol %) solid loading.

Example 20

This example provides a description of making and characterizing nanozirconia gels of the present disclosure.

The 2ESD zirconia suspension attrition milling and gel preparation steps were identical to Example 7 with osmotic time of 16 hours and smaller MWCO dialysis membrane tubing (MWCO 1000). However, after attrition milling and before placing the suspension to dialysis tubing, 1.0% by weight to solid zirconia of PEG35K was admixed to the suspension, followed by 0.05% by weight to solid zirconia of polyacrylic acid (PAA). After being shaken and homogenized, the mixture was then loaded in dialysis tubing and osmosized for 16 hours. The obtained gel was translucent and soft to semi-soft, with 75 wt % (33.0 vol %) solid loading.

Example 21

This example provides a description of making and characterizing nanozirconia gels, intermediate materials, and dental restorations of the present disclosure.

Example 22

This example provides a description of making and characterizing nanozirconia gels, intermediate materials, and dental restorations of the present disclosure.

Gel prepared from Example 3A was centrifugal cast and dried as describe in Example 1. The obtained green bodies were cylinders with ~32 mm in diameter and 14-18 mm in height and free of cracks or bubbles by visual examination. One of the sides of these cylindrically shaped blanks was flattened and glued to Katana-compatible mandrel by superglue. Katana Dental CAD/CAM System (Model H18) was used to mill these green blanks into standard molar crowns using enlargement factor of 1.15-1.2. The obtained crack-free green crowns were then subjected to organics burn-out by heating at a rate of 0.1° C./min to 240° C., then 0.5° C./min to 700° C. and holding for 2 hours at that temperature resulting in a crack free "brown" crowns. The "brown" crowns were then sintered at a ramp rate of 3° C./min to 1100° C., hold for 2 hours. The as-sintered molar crowns were then glazed (Example 22A) or stained and glazed to match Vita A3 shade guide. The sample information is summarized in Table 5.

Example 23

This example provides a description of making and characterizing nanozirconia gels and zirconia green bodies of the present disclosure.

This example is identical to Example 7 except for a longer osmotic time (24 hours vs. 22 hours) when gel was prepared.

The longer osmotic time has increased the gel loading from 77 wt % (Example 7) to 80 wt % (Example 23), which resulted in the gel turning from semi-soft (Example 7) to semi-rigid/rigid (Example 23). The obtained gel was thus non-formable. This example demonstrated that the gel formability is highly related to gel loading, which can be controlled by osmotic time. The gel solid loading, gel softness and gel formability are presented and compared in Table 6.

This example is identical to Example 9 except for a longer osmotic time (22 hours vs. 19 hours) when gel was prepared. The longer osmotic time has increased the gel loading from 75 wt % (Example 9) to 77 wt % (Example 25). Both gels were in the range of soft to semi-soft but the gel in example 9 was softer due to the lower solid loading. The gel solid loading, gel softness, gel formability and green body survival rate are presented in and compared Table 6.

TABLE 6

Comparison of 2ESD gels with different gel solid loading.

| Gel | Processing agent | Osmotic time, hr | Gel loading, wt % (vol %) | Gel softness/rigidity | Gel formability ranking | PEG35K vs PEG20K | Green body drying survival rate, % |
|---|---|---|---|---|---|---|---|
| 2ESD with higher solid loading | EX23: No processing agent | 24 | ~80 (39.6) | semi-rigid to rigid | 0 | | N/A |
| | EX24: 1.0% PEG | 24 | ~76 (34.2) | soft to semi-soft | 3 | EX24A: 35k | 0 |
| | | | | | | EX24B: 20k | 0 |
| | EX25: 1.0% PEG + 0.05% PVA | 22 | ~77 (35.4) | soft to semi-soft | 3 | EX25A: 35k | 0 |
| | | | | | | EX25B: 20k | 0 |
| | EX26: 0.5% PEG + 0.05% PVA | 20 | ~78 (36.8) | semi-soft | 2 | EX26A 35k | 0 |
| | | | | | | EX26B: 20k | 0 |
| | EX27: 0.1% PEG + 0.05% PVA | 18 | ~78 (36.8) | semi-soft t to semi-rigid | 0-1 | EX27A: 35k | 0 |
| | | | | | | EX27B: 20k | 0 |
| 2ESD with lower solid loading | EX7: No processing agent | 22 | ~77 (35.4) | semi-soft | 2-3 | | 0 |
| | EX8: 1.0% PEG | 22 | ~75 (33.0) | soft to semi-soft | 3 | EX8A: 35k | >80 |
| | | | | | | EX8B: 20k | >80 |
| | EX9: 1.0% PEG + 0.05% PVA | 19 | ~75 (33.0) | soft to semi-soft | 3 | EX9A: 35k | >80 |
| | | | | | | EX9B: 20k | <70 |
| | EX10: 0.5% PEG + 0.05% PVA | 19 | ~76 (34.2) | semi-soft | 2-3 | EX10A: 35k | <70 |
| | | | | | | EX10B: 20k | <70 |
| | EX11: 0.1% PEG + 0.05% PVA | 18 | ~76 (34.2) | semi-soft | 2 | EX11A: 35k | >80 |
| | | | | | | EX11B: 20k | <70 |

Example 24

This example provides a description of making and characterizing nanozirconia gels and zirconia green bodies of the present disclosure.

This example is identical to Example 8 except for a longer osmotic time (24 hours vs. 22 hours) when gel was prepared. The longer osmotic time has increased the gel loading from 75 wt % (Example 8) to 76 wt % (Example 24). Both gels were in the range of soft to semi-soft but the gel in example 8 was a little softer due to the lower solid loading. The gel solid loading, gel softness, gel formability and green body survival rate are presented in and compared Table 6.

Example 25

This example provides a description of making and characterizing nanozirconia gels and zirconia green bodies of the present disclosure.

Example 26

This example provides a description of making and characterizing nanozirconia gels and zirconia green bodies of the present disclosure.

This example is identical to Example 10 except for a longer osmotic time (20 hours vs. 19 hours) when gel was prepared. The longer osmotic time has increased the gel loading from 76 wt % (Example 10) to 78 wt % (Example 25). Both gels were in the range of semi-soft but the gel in example 10 was softer due to the lower solid loading. The gel solid loading, gel softness, gel formability and green body survival rate are presented in and compared Table 6.

Example 27

This example provides a description of making and characterizing nanozirconia gels and zirconia green bodies of the present disclosure.

This example is identical to Example 11 with the same osmotic time (18 hours) when gel was prepared. However, the gel prepared from this example is 2 wt % higher in solid loading than that from example 11 (78 wt % vs. 76 wt %). The reason is not clear at this time but it could be due to the relatively lower suspension to osmotic solution volume ratio specifically in Example 27. The 2 wt % higher solid loading resulted in the gel turned from semi-soft (example 11) to semi-rigid (Example 27) and led to different results of survival rate as indicated in Table 6.

Example 28

This example provides a description of making and characterizing nanozirconia gels of the present disclosure.

Gels prepared from Example 1, 2A, 5A (2TODA suspension) and Example 23, 8A, 11A (2ESD suspension) were characterized with a Kinexus Ultra+ Rotational Rheometer by Malvern, to measure their yield stresses and shear rate dependent viscosities. All tests were done at 25° C. 25 mm roughened parallel plates were employed to provide improved adhesion to hold the gel samples. A liquid seal enclosure was used to provide a humid environment to avoid gel drying during the tests. The thickness of the gel samples (working gap between plates) were controlled by a fixed normal load of 5 N. The rheometry measurement was conducted by gradually increasing the shear stress from 5 Pa to a maximum of 10,000 Pa at a rate of 10 Pa per second. The testing results are presented in FIGS. 7A, 7B, 8A, and 8B, and the yield stress and viscosity at yield point of each gel are summarized in Table 1A.

Example 29

This example provides a description of making and characterizing nanozirconia gels and zirconia green bodies of the present disclosure.

Vickers hardness (HV) measurements were conducted on dried green bodies formed with different forming methods, including drop casting nanozirconia suspensions (comparative example 1), centrifugal casting nanozirconia gels (Example 1 an Example 5A) and CIP-ing conventional zirconia powders (Zirlux® FC2 Green discs). A Mitutoyo HV-112 indentation hardness testing machine was used for the measurements. Sample hardness was measured at different load levels of 1.0, 2.5, 5.0, and 10.0 kg force. All samples were 7-8 mm in thickness and at least 10 times thicker than the indentation diagonals with at least 5 indentation diagonals of spacing between indents. Five consecutive measurements were conducted on each sample and the results are summarized in Table 7.

TABLE 7

Comparison of Vickers hardness of different green bodies.

Vickers Hardness (HV), kg/mm$^2$
Average ± Standard Deviation for five consecutive measurements. All samples were 7-8 mm in thickness (sample thickness is given in brackets below) and at least 10 times thicker than the indentation diagonal with at least 5 indentation diagonals of spacing between indents.

| Load, kg | Zirlux FC2 disc CIP-ed at 380 MPa (commercial product tested in green stage prior to soft sintering to HV of 50-70 kg/mm$^2$) | Drop cast No processing agent (7.7 mm) | Centrifugally cast using formable nanozirconia gel | |
|---|---|---|---|---|
| | | | No processing agent (7.7 mm) | 0.1% PEG35K + 0.05% PVA*** (7.4 mm) |
| 1.0 | 24.3 ± 0.2 | 19.0 ± 0.8 | 42.5 ± 0.6 | 43.2 ± 0.2 |
| 2.5 | 24.3 ± 0.2 | 18.9 ± 0.5 | 46.3 ± 0.5 | 45.0 ± 0.2 |
| 5.0 | — | 20.0 ± 0.5/19.5** | 44.3 ± 0.3 | 46.5 ± 0.3 |
| 10.0* | 24.5 ± 0.1 | Samples cracked into multiple pieces | 44.8 ± 0.6 | 46.4 ± 0.2 |

*Surviving test at 10 kg load is necessary condition for machinability as peak milling loads are higher
**Average for two measurements on one of the samples which cracked even at 5 kg load during the third consecutive measurement
***Confirmed millable Example 30

This example provides a description of making and characterizing "brown" bodies of the present disclosure.

Figure 14:
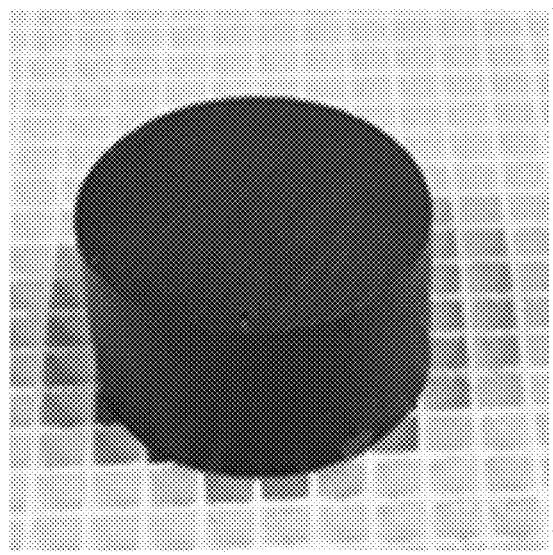
FIG. 14. An example of a "brown" body as described in Example 30. The brown color resulted from the oxidation of organics (TODA processing agent) in the green body when heated to 200° C. during the debinding process. The color was removed when "brown" body was heated to a temperature above 500° C.

While typically brown blanks are translucent as shown in FIG. 3 they can be made black or brown and totally impermeable to light indicating incomplete removal of organics. That where the term "brown body" originally came from. Most of the times these samples are irreversibly lost due to ash/soot formation within the pores. Noteworthy that in some cases brown color shown in FIG. 14 can be reversible and still produce redeemable brown bodies. It is speculated that the brown color of this sample was resulted from the oxidation of organics (TODA processing agent) in the green body.

Example 31

This example provides a description of making and characterizing nanozirconia gels of the present disclosure.

Gels prepared from Examples 1, 4A and 5A were characterized with Agilent Cary 100 UV-Visible Spectrophotometer G9821A to measure the transmittance, and Minolta CM3610D Spectrophotometer to measure the opalescence. The gels were placed between two 2" diameter quartz discs while 1.4 mm thick spacers was used to control the gel thickness. The measurement results are summarized in Table 8.

TABLE 8

Optical properties of examples of gels.

| Examples (Thickness is 1.4 mm) | 2TODA, processing agent | Total forward Transmittance (%) @560 nm wavelength | In-line Transmittance(%) @560 nm wavelength | Opalescence parameter |
|---|---|---|---|---|
| EX1 | No processing agent | 72.4 | 58.9 | 26.4 |
| EX4A | 0.05PVA + 0.5PEG35k | 76.5 | 52.8 | 28.0 |
| EX5A | 0.05PVA + 0.1PEG35k | 75.8 | 61.8 | 28.4 |

Example 32

This example provides a description of making and characterizing zirconia green bodies of the present disclosure.

Green body cylinders prepared from Example 4A, 5A and 4B were cut, ground, and polished to make 2.0 mm thick discs-shaped samples for transmittance and opalescence measurements using the same equipment of Example 31. The measurement results are summarized in Table 9.

TABLE 9

Optical properties of examples of green bodies.

| Examples (Thickness is 2.0 mm) | 2TODA, processing agent | Total forward Transmittance (%) @560 nm wavelength | Opalescence parameter |
|---|---|---|---|
| EX4A | 0.05PVA + 0.5PEG35k | 46.9 | 20.9 |
| EX5A | 0.05PVA + 0.1PEG35k | 47.8 | 21.1 |
| EX4B | 0.05PVA + 0.5PEG20k | 48.4 | 19.9 |

Example 33

This example provides a description of making and characterizing zirconia brown bodies of the present disclosure.

Disc-shaped brown/pre-sintered bodies were prepared by heating green body discs of Example 31 to 550° C. and cooling down to room temperature, for transmittance and opalescence measurements using the same equipment of Example 31. The measurement results are summarized in Table 10.

TABLE 10

Optical properties of examples of brown bodies.

| Example (Thickness is 2.0 mm) | 2TODA, processing agent | Total forward Transmittance (%) @560 nm wavelength | Opalescence parameter |
|---|---|---|---|
| EX4A | 0.05PVA + 0.5PEG35k | 43.4 | 29.0 |
| EX5A | 0.05PVA + 0.1PEG35k | 44.3 | 28.3 |
| EX4B | 0.05PVA + 0.5PEG20k | 43.9 | 28.5 |

Example 34

This example provides a description of making and characterizing nanozirconia gels of the present disclosure.

Gels prepared from Example 1, 4A and 5A were diluted with water to 0.5 wt % loading. Particle size and size distribution were measured with Malvern Nano-ZS zetasizer. The measurement results are compared with those of the original suspension used to make the gel, as shown in Table 11.

TABLE 11

Example of redispersibility of gels.

| | Volume Average D, nm | |
|---|---|---|
| Processing agent(s) | Suspension | Gel |
| No processing agent (EX1) | 22.9 ± 1.4 | 23.5 ± 4.3 |
| 0.5% PEG35K + 0.05% PVA (EX4A) | 22.8 ± 1.5 | 25.3 ± 3.3 |
| 0.1% PEG35K + 0.05% PVA (EX5A) | 23.2 ± 1.3 | 22.1 ± 4.1 |

The invention claimed is:

1. A gel comprising a plurality of zirconia nanoparticles and water, wherein the zirconia nanoparticles have an average size of 10 to 30 nm, 95% or more of the zirconia nanoparticles by volume have a size of 45 nm or less, the zirconia nanoparticles are present at 70 to 85% by weight based on the total weight of the gel, and wherein the gel further comprises a processing agent and the processing agent is 2% by weight 2-[2-(2-methoxyethoxy)ethoxy]acetic acid (TODA) and/or electrostatic colloid stabilizer (ESD) and 0.1% by weight polyethylene glycol having a molecular weight of 35,000 g/mol (PEG35K) and 0.05% by weight polyvinylalcohol (PVA) or 0.5% percent by weight PEG35k and 0.05% by weight PVA, wherein the percent by weight values are based on the total weight of the nanoparticles in the gel.

2. The gel of claim 1, wherein:
   i) 99% of nanoparticles by volume have a size less than 60 nm±10 nm;
   ii) 95% of nanoparticles by volume have a size less than 40 nm±5 nm;
   iii) 50% of nanoparticles by volume have a size less than 20 nm±5 nm; and
   iv.) 5% of nanoparticles by volume have a size less than 12 nm±3 nm.

3. The gel of claim 1, wherein 95% or greater by volume of the zirconia nanoparticles comprise 1 to 5 crystallites.

4. The gel of claim 1, wherein the amount of the processing agent is 1.5 to 3.3% by weight based on the total weight of the nanoparticles in the gel.

5. The gel of claim 1, wherein the gel is translucent and has a transmittance at 560 nm wavelength of 60 to 80% for a 1 to 2 mm thick sample of the gel.

6. The gel of claim 1, wherein the gel has an opalescence of 20 to 30 for a 1 to 2 mm thick sample of the gel.

7. The gel of claim 1, wherein the gel is redispersible in an aqueous medium.

8. The gel of claim 1, wherein the zirconia nanoparticles are in a tetragonal phase.

9. The gel of claim 1, wherein 10% or less of the zirconia nanoparticles are in a cubic and/or a monoclinic phase.

10. The gel of claim 1, wherein the gel exhibits a viscosity at yield point of $1 \times 10^9$ to $12 \times 10^9$ mPa·s.

11. The gel of claim 1, wherein the gel exhibits a yield stress of $1\times10^3$ to $9\times10^3$ Pa.

12. The gel of claim 1, wherein the gel is formable into a free-standing three-dimensional shape.

* * * * *